(12) United States Patent
Muir et al.

(10) Patent No.: US 7,419,954 B2
(45) Date of Patent: *Sep. 2, 2008

(54) STAPHYLOCOCCUS PEPTIDES FOR BACTERIAL INTERFERENCE

(75) Inventors: Tom W. Muir, New York, NY (US); Patricia Mayville, Robbinsville, NJ (US); Richard P. Novick, New York, NY (US); Ronald Beavis, Winnipeg (CA); Guangyong Ji, Rockville, MD (US)

(73) Assignee: The Rockefeller University, New York, NY (US)

( * ) Notice: Subject to any disclaimer, the term of this patent is extended or adjusted under 35 U.S.C. 154(b) by 320 days.

This patent is subject to a terminal disclaimer.

(21) Appl. No.: 11/212,020

(22) Filed: Aug. 25, 2005

(65) Prior Publication Data

US 2007/0185016 A1 Aug. 9, 2007

Related U.S. Application Data

(63) Continuation-in-part of application No. 10/032,950, filed on Dec. 27, 2001, now Pat. No. 6,953,833, which is a continuation of application No. 09/339,511, filed on Jun. 24, 1999, now Pat. No. 6,337,385.

(60) Provisional application No. 60/090,402, filed on Jun. 24, 1998.

(51) Int. Cl.
*A61K 38/00* (2006.01)
*A61K 38/12* (2006.01)

(52) U.S. Cl. .............................. 514/9; 514/11; 514/13; 514/18; 530/317

(58) Field of Classification Search ............ 514/9, 514/11, 13, 18; 530/317, 323, 331
See application file for complete search history.

(56) References Cited

U.S. PATENT DOCUMENTS 5,616,320 A * 4/1997 Argoudelis et al. ......... 424/115

6,953,833 B2 * 10/2005 Muir et al. .................. 530/317

OTHER PUBLICATIONS

Wright et al., Transient interference with *Staphylococcal quorum* sensing blocks abscess formation, Proc. Natl. Acad Sci., 102:1691-1696 (2005).

* cited by examiner

*Primary Examiner*—Jon P Weber
*Assistant Examiner*—Rita Mitra
(74) *Attorney, Agent, or Firm*—Klauber & Jackson LLP

(57) ABSTRACT

The present invention provides a cyclic peptide comprising the structure:

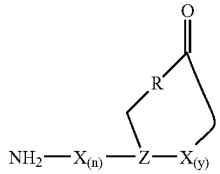

wherein X is selected from the group consisting of an amino acid, an amino acid analog, a peptidomimetic and a non-amide isostere, Z is selected from the group consisting of a synthetic amino acid and a biosynthetic amino acid, R is selected from the group consisting of oxygen, nitrogen, sulfur and carbon, n is 0 to 10 and y is 1 to 10. The present invention also provides a cyclic peptide comprising the amino acid sequence of $NH_2-X_{(n)}-Z-X_{(y)}$—COOH and a cyclic bond between the Z residue and COOH other than a thioester bond, wherein X is selected from the group consisting of to an amino acid, an amino acid analog, a peptidomimetic and a non-amide isostere, Z is selected from the group consisting of a synthetic amino acid and a biosynthetic amino acid, n is 0 to 10 and y is 1 to 10. Methods of preparation including a cyclization protocol, and methods of use of the cyclic peptides of the invention are also disclosed.

12 Claims, 10 Drawing Sheets

Fig. 2C

| AgrDII Peptide Variant | Activation (ED$_{50}$ nM) Group II Cells | Inhibition (IC$_{50}$ nM) Group I Cells | Inhibition (IC$_{50}$ nM) Group II Cells | Inhibition (IC$_{50}$ nM) Group III Cells |
|---|---|---|---|---|
| Ala 1 (Gly to Ala) | 31 | <1 | None | Not determined |
| Ala 2 (Val to Ala) | 73 | <1 | None | Not determined |
| Ala 3 (Asn to Ala) | None | <1 | None | Not determined |
| Ala 6 (Ser to Ala) | 63 | <<1 | None | Not determined |
| Ala 7 (Ser to Ala) | <1 | <1 | None | Not determined |
| Ala 8 (Leu to Ala) | None | None | None | Not determined |
| Ala 9 (Phe to Ala) | None | None | None | Not determined |

Fig. 5A *agr*-II reporter

Fig. 5B *agr*-II reporter

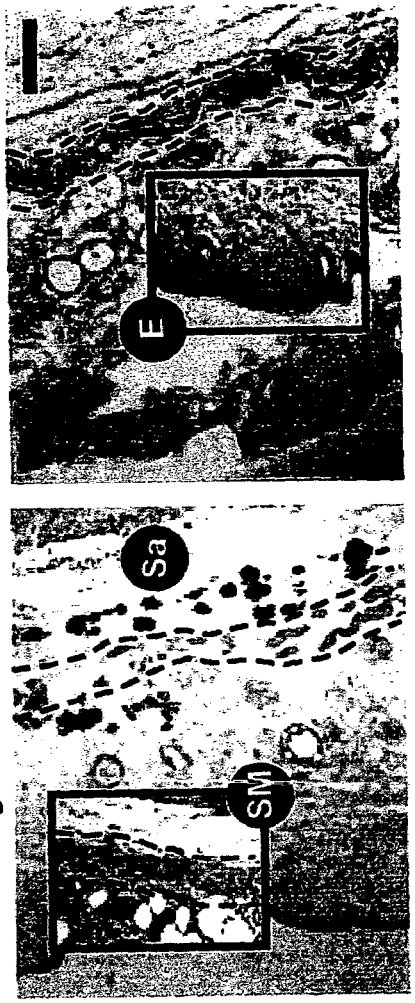
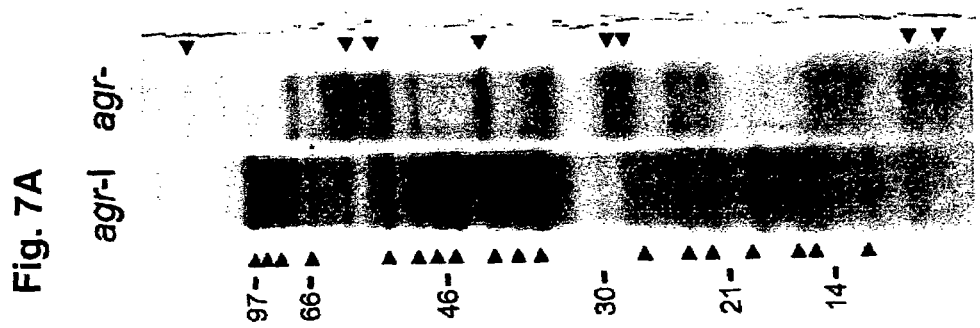
Fig. 7A
Fig. 7B
Fig. 7C

SEQUENCE LISTING

```
<160> NUMBER OF SEQ ID NOS: 8

<210> SEQ ID NO 1
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: VARIANT
<222> LOCATION: (5)
<223> OTHER INFORMATION: Xaa represents any amino acid at this position.

<400> SEQUENCE: 1

Gly Val Asn Ala Xaa Ser Ser Leu Phe
  1               5

<210> SEQ ID NO 2
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: VARIANT
<222> LOCATION: (5)
<223> OTHER INFORMATION: Xaa represents any amino acid at this position.

<400> SEQUENCE: 2

Gly Ala Asn Ala Xaa Ser Ser Leu Phe
  1               5

<210> SEQ ID NO 3
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

-continued

```
<221> NAME/KEY: VARIANT
<222> LOCATION: (5)
<223> OTHER INFORMATION: Xaa represents any amino acid at this position.

<400> SEQUENCE: 3

Gly Val Ala Ala Xaa Ser Ser Leu Phe
 1               5

<210> SEQ ID NO 4
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: VARIANT
<222> LOCATION: (5)
<223> OTHER INFORMATION: Xaa represents any amino acid at this position.

<400> SEQUENCE: 4

Ala Val Asn Ala Xaa Ser Ser Leu Phe
 1               5

<210> SEQ ID NO 5
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: VARIANT
<222> LOCATION: (5)
<223> OTHER INFORMATION: Xaa represents any amino acid at this position.

<400> SEQUENCE: 5

Gly Val Asn Ala Xaa Ala Ser Leu Phe
 1               5

<210> SEQ ID NO 6
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: VARIANT
<222> LOCATION: (5)
<223> OTHER INFORMATION: Xaa represents any amino acid at this position.

<400> SEQUENCE: 6

Gly Val Asn Ala Xaa Ser Ala Leu Phe
 1               5

<210> SEQ ID NO 7
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: VARIANT
<222> LOCATION: (5)
<223> OTHER INFORMATION: Xaa represents any amino acid at this position.

<400> SEQUENCE: 7

Gly Val Asn Ala Xaa Ser Ser Ala Phe
```

```
<210> SEQ ID NO 8
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: VARIANT
<222> LOCATION: (1)
<223> OTHER INFORMATION: Xaa represents any amino acid at this position.

<400> SEQUENCE: 8

Xaa Ser Ser Leu Phe
 1               5
```

US 7,419,954 B2

STAPHYLOCOCCUS PEPTIDES FOR BACTERIAL INTERFERENCE

CROSS REFERENCE TO RELATED APPLICATION

The present invention is a continuation in part of U.S. application Ser. No. 10/032,950, filed Dec. 27, 2001, now U.S. Pat. No. 6,953,833, issued Oct. 11, 2005, which is a continuation of application Ser. No. 09/339,511, filed Jun. 24, 1999, now U.S. Pat. No. 6,337 385, issued Jan. 8, 2002, which, in turn claims priority from Provisional Application Ser. No. 60/090,402, filed Jun. 24, 1998. Priority under 35 U.S.C §§119 and 120 is claimed, and the entire contents of each of the above applications are incorporated herein by reference in their entireties.

FIELD OF THE INVENTION

The present invention relates generally to synthetic, cyclic peptides for bacterial interference. The invention also encompasses methods for treating diseases or conditions associated with bacterial infections, wherein the peptides of the invention and compositions comprising these peptides are administered to a subject or patient in a therapeutically effective amount to treat the disease or condition.

BACKGROUND OF THE INVENTION

Several publications and patent documents are referenced in this application in order to more fully describe the state of the art to which this invention pertains. The disclosure of each of these publications and documents is incorporated by reference herein. The Sequence Listing is provided at the end of the Specification and before the claims.

*Staphylococcus aureus* (*S. aureus*) is an important pathogen in humans which is now under increasing risk of developing antibiotic resistance to currently available therapeutics. Consequently, there is a pressing need to identify new types of antibiotic agents effective against these drug resistant bacterial strains. The phenomenon of 'bacterial interference' may provide as yet unexplored avenues for the design of these new therapeutics. Bacterial interference refers to the ability of one organism to disrupt the biological functions of another. Until recently this survival process was thought to occur solely through a growth inhibition mechanism (Ji et al. (1997) *Science* 276, 2027-30), however a novel type of bacterial interference in *S. aureus* has been described which involves the inhibition of the so-called agr response (Novick et al. (1995) *Mol. Gen. Genet*. 248, 446-58; Morfeldt et al. (1995) *EMBO J*. 14:4569-4577). This process is mediated by short secreted peptides containing a putative thiololactone ring structure. Chemical synthesis confirms that the native Agr peptides contain a thiololactone moiety, and that this structure is absolutely necessary for full biological activity. In addition, structure-activity studies are described by the present invention which offer insights into the nature of the agr activation and inhibition mechanisms.

Accessory genes allow bacteria to survive and multiply in plant or animal hosts. In *S. aureus* these virulence factors (cytotoxins and tissue-degrading enzymes) are under the control of the agr locus which contains two divergent promoters, P2 and P3. The RNA transcript from the P3 promoter is responsible for the upregulation of secreted virulence factors as well as the downregulation of surface proteins, the agr response (Novick et al. (1993) *EMBO J*. 12, 3967-75; Morfeldt et al. (1995) *EMBO J*. 14:4569-4577). There are four genes, agrA-D, in the P2 operon which code for the cytosolic, transmembrane and extracellular components of a density-sensing/autoinduction circuit (Novick et al. (1995) supra).

The product of the agrD gene is a pro-peptide which is processed and secreted through AgrB, an integral membrane protein. The active AgrD peptide is then thought to bind to the transmembrane receptor by the agrC gene. Binding of the AgrD peptide triggers a standard two-component signal transduction pathway in which the AgrC receptor becomes autophosphorylated on a histidine residue leading to subsequent trans-phosphorylation of the AgrA gene product. Phosphorylated AgrA then activates transcription from the P2 and P3 agr promoters (Novick et al. (1995) supra).

*S. aureus* strains can be divided into a least three groups (Ji et al. (1997) supra), each of whose secreted AgrD peptide can activate the agr response within the same group and inhibit the agr response in strains belonging to the other groups. It is the latter effect that constitutes a novel form of bacterial interference (Ji et al. (1997) supra). The AgrD autoinducing peptides, generated following processing and secretion through AgrB, consist of seven to nine residues. Interestingly, the sequences are highly variable among the groups, although all contain a conserved cysteine residue 5 amino acids from the C-terminus. Mass spectrometric analysis of AgrD peptides isolated from culture supernatants indicated a mass discrepancy of −18 Da compared to the predicted masses based on the peptide sequences (Ji et al. (1995) *Proc. Natl. Acad. Sci. USA* 92, 12055-9). This observation combined with the presence of the conserved cysteine residue in AgrD peptides, has led to the suggestion that these secreted peptides contain an intramolecular thiol ester linkage between the cysteine sulfhydryl group and the carboxy-terminus (Ji et al. (1997) supra). Consistent with this thiololactone structure, the addition of hydroxylamine to a purified AgrD peptide was observed to abolish its biological activity (Ji et al. (1997) supra).

The inability to isolate significant quantities of secreted AgrD peptides means that very little is known about the biochemistry of the AgrD/AgrC interaction. For example, the potency of the AgrD peptide in either activating (within *S. aureus* strains of the same group) or inhibiting (in *S. aureus* strains from other groups) the agr response is unknown. Equally, it is essential to determine whether the putative thiololactone structure within the AgrD peptides is required for activation of the agr response, inhibition of the agr response or both. The present disclosure provides such elucidation. The study detailed herein confirms the presence of the thiololactone moiety within the AgrD peptides through total chemical synthesis. Having demonstrated synthetic access to the system, more rigorous biochemical and structure-activity studies on the AgrD/AgrC interaction are addressed. The present disclosure further delineates that elimination of the thiol ester component of the cyclic ring structure can destroy activity activating the agr response while preserving (and enhancing) inhibitory activity.

SUMMARY OF THE INVENTION

The present invention provides a cyclic peptide comprising the structure:

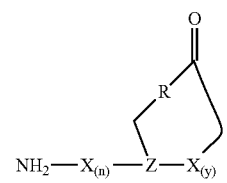

wherein X is selected from the group consisting of an amino acid, an amino acid analog, a peptidomimetic and a non-amide isostere, Z is selected from the group consisting of a synthetic amino acid and a biosynthetic amino acid, R is selected from the group consisting of oxygen, nitrogen, sulfur and carbon, n is 0 to 10 and y is 1 to 10. The invention also contemplates a peptide composition comprising the provided cyclic peptide and a carrier.

The present invention also provides a cyclic peptide comprising the amino acid sequence of $NH_2$—$X_{(n)}$-Z-$X_{(y)}$—COOH and a cyclic bond between the Z residue and COOH other than a thioester bond, wherein X is selected from the group consisting of an amino acid, an amino acid analog, a peptidomimetic and a non-amide isostere, Z is selected from the group consisting of a synthetic amino acid and a biosynthetic amino acid, n, is 0 to 10 and y is 1 to 10. The invention also contemplates a peptide composition comprising the provided cyclic peptide and a carrier, as well as therapeutic methods for treatment of infection that involve the administration of the pharmaceutical compositions that are and may be prepared in accordance with the teachings of the invention herein. Yet further, the invention extends to methods for the preparation of the cyclic peptide involving a cyclization protocol that is described in further detail herein and is illustrated in Example 1 and in FIG. 1A, and that itself is inventive.

Accordingly, it is a principal object of the present invention to provide a cyclic peptide comprising the amino acid sequence of $NH_2$—$X_{(n)}$-Z-$X_{(y)}$—COOH and a cyclic bond between the Z residue and COOH other than a thioester bond, wherein X is selected from the group consisting of an amino acid, an amino acid analog, a peptidomimetic and a non-amide isostere, Z is selected from the group consisting of a synthetic amino acid and a biosynthetic amino acid, n is 0 to 10 and y is 1 to 10.

It is a further object of the present invention to provide a cyclic peptide comprising the amino acid sequence of $NH_2$—$X_{(n)}$-Z-$X_{(y)}$—COOH and a cyclic bond between the Z residue and COOH other than a thioester bond, wherein X is selected from the group consisting of an amino acid, an amino acid analog, a peptidomimetic and a non-amide isostere, Z is selected from the group consisting of a synthetic amino acid and a biosynthetic amino acid, n is 0 to 10 and y is 1 to 10, that is devoid of activating activity and which retains inhibitory activity.

It is yet a further object of the present invention to provide a cyclic peptide comprising the amino acid sequence of $NH_2$—$X_{(n)}$-Z-$X_{(y)}$—COOH and a cyclic bond between the Z residue and COOH other than a thioester bond, wherein X is selected from the group consisting of an amino acid, an amino acid analog, a peptidomimetic and a non-amide isostere, Z is selected from the group consisting of a synthetic amino acid and a biosynthetic amino acid, n is 0 to 10 and y is 1 to 10, wherein the bond is a selected from the group consisting of a lactam ring and a lactone ring.

It is a still further object of the present invention to provide a pharmaceutical composition which comprises the provided peptides and a pharmaceutically acceptable carrier.

It is yet another object of the present invention to provide a method for the treatment of an S. aureus infection in a subject comprising administering to the subject the provided peptides in an amount effective to treat the infection in the subject. It is to be understood that the provided peptides may be administered in a pharmaceutical composition appropriate for the intended application.

S. aureus infections are known to cause a wide variety of conditions that range from relatively benign infections of the skin (e.g., folliculitis) to serious and even life-threatening disease (e.g., osteomyelitis, endocarditis, septic arthritis, and toxic shock syndrome). Moreover, S. aureus strains are considered the leading cause of primary infections originating in hospitals (nosocomial infections) in the United States. Further and potentially lethal complications arise when such an infection is caused by a strain that is resistant to many of the commonly used antibiotics. Such strains are more prevalent in hospitals because of the widespread use of antibiotics to treat patients. The increasing resistance of S. aureus to currently available antimicrobial agents is illustrated by the recent appearance of strains with reduced susceptibility to vancomycin. These trends underscore the urgent need to develop alternative protocols for the treatment and prevention of staphylococcal disease.

Accordingly, the present invention is directed to using the peptides and pharmaceutical compositions of the invention, either alone or in conjunction with antibiotic regimens, to treat a subject suffering from a condition or disease associated with an S. aureus infection.

In one aspect, the invention encompasses a method for treating an S. aureus infection in a subject comprising administering to the subject an amount of a cyclic peptide effective to treat the infection, said cyclic peptide comprising the structure:

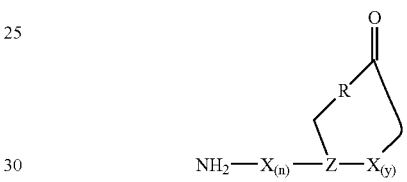

wherein X is selected from the group consisting of an amino acid, an amino acid analog, a peptidomimetic and a non-amide isostere, Z is selected from the group consisting of a synthetic amino acid and a biosynthetic amino acid, R is selected from the group consisting of oxygen, nitrogen, sulfur and carbon, n is 0 to 10 and y is 1 to 10, wherein said cyclic peptide is administered in an effective amount to achieve a clinically significant reduction in said S. aureus infection, said method further comprising administering to the subject a therapeutically effective amount of at least one antibiotic.

In another aspect, the invention is directed to a method for treating an S. aureus infection in a subject comprising administering to the subject an amount of a cyclic peptide effective to treat the infection, said cyclic peptide comprising the amino acid sequence of $NH_2$—$X_{(n)}$-Z-$X_{(y)}$—COOH and a cyclic bond between the Z residue and COOH other than a thioester bond, wherein X is selected from the group consisting of an amino acid, an amino acid analog, a peptidomimetic and a non-amide isostere, Z is selected from the group consisting of a synthetic amino acid and a biosynthetic amino acid, n is 0 to 10 and y is 1 to 10, wherein said cyclic peptide is administered in an effective amount to achieve a clinically significant reduction in said S. aureus infection, said method further comprising administering to the subject a therapeutically effective amount of at least one antibiotic.

The cyclic peptides of the invention may be administered cutaneously, subcutaneously, intravenously, parenterally, orally, topically, or by aerosol in an effective amount to achieve a clinically significant reduction in said S. aureus infection. In one embodiment, a cyclic peptide of the invention and at least one antibiotic are administered via different routes. The cyclic peptide may be administered locally, for example, while the at least one antibiotic is administered systemically. Alternatively, the cyclic peptide and at least one antibiotic may be administered via the same route; both may, for example, be administered either locally or systemically.

The present invention also encompasses methods wherein the cyclic peptide and at least one antibiotic are administered via the same route and supplemented with additional administration of either the cyclic peptide and/or at least one antibiotic via an alternative or different route. It is to be understood in all of these aspects of the invention, the cyclic peptide and at least one antibiotic may be administered concomitantly or at different times.

In an embodiment of the invention, the method is directed to treating an S. aureus infection in a subject comprising administering to the subject an amount of a cyclic peptide, wherein Z has a side chain comprising oxygen, nitrogen or carbon.

In another aspect, the method of the invention is directed to treating an S. aureus infection in a subject comprising administering to the subject an amount of a cyclic peptide, wherein the cyclic bond is a lactam or lactone bond.

In yet another aspect of the invention, the method utilizes a cyclic peptide that inhibits the agr response.

In another embodiment, the method of the invention is directed to treating an S. aureus infection in a subject comprising administering to the subject an amount of a cyclic peptide, wherein y is 4.

In an aspect of the invention, the cyclic peptide is selected from the group of peptides having an amino acid sequence that comprises SEQ ID NO: 1, SEQ ID NO: 2, SEQ ID NO: 3, SEQ ID NO: 4, SEQ ID NO: 5, SEQ ID NO: 6, SEQ ID NO: 7 and SEQ ID NO: 8.

The method of the invention encompasses treating an S. aureus infection in a subject comprising administering to the subject a composition comprising at least one cyclic peptide of the invention, at least one antibiotic and a carrier. In an aspect of the invention, the composition administered is a pharmaceutical composition comprising at least one cyclic peptide of the invention, at least one antibiotic and a pharmaceutically acceptable carrier. Such pharmaceutically acceptable carriers include, but are not limited to, a diluent, an aerosol, a topical carrier, an aqueous solution, a nonaqueous solution, and a solid carrier. It is to be understood that the cyclic peptide of the invention and the at least one antibiotic may also be administered in separate compositions to a subject in need thereof.

The present invention also encompasses a composition comprising at least one cyclic peptide of the invention, at least one antibiotic and a carrier. In a particular aspect, the present invention encompasses a pharmaceutical composition comprising a cyclic peptide of the invention, at least one antibiotic and a pharmaceutically acceptable carrier.

The method of the invention may be used advantageously when the S. aureus infection causes a site of localized, sequestered, or encapsulated infection, said method comprising draining or treating the site of localized infection to produce a treated site and administering said cyclic peptide directly to said treated site. In an aspect of the invention, the antibiotic(s) are also administered directly to the treated site. Exemplary sites of localized, sequestered, or encapsulated infections include, but are not limited to: abscesses (e.g., superficial and deep tissue), regions of bone affected by osteomyelitis, regions of the heart affected by endocarditis, and joints affected by septic arthritis.

The cyclic peptides of the invention and compositions thereof may also be used advantageously in methods for pre-treating devices intended for implantation (e.g., orthopaedic implants, heart valves) prior to their insertion into a subject in need of such a device. Such pre-treatment will delay, if not prevent biofilm formation on the implanted device, thereby preventing subsequent infection of the implanted biomaterial which generally results in serious clinical complications for the recipient of the implant.

The cyclic peptides of the invention may also be used to advantage to treat patients with S. aureus infections that exhibit antibiotic resistance.

It is a still further object of the invention to provide methods for the preparation of the cyclic peptides of the invention that involve a solid phase cyclization protocol as illustrated and described herein.

Other objects and advantages will become apparent to those skilled in the art from a review of the ensuing description which proceeds with reference to the following illustrative drawings.

BRIEF DESCRIPTION OF THE FIGURES

FIG. 1A. Generation of thiololactone peptides via a solid phase intramolecular chemical ligation strategy. FIG. 1B. Reverse-phase HPLC of the crude reaction mixture from the AgrDI peptide synthesis. Inset shows the electrospray mass spectrum (ESMS) obtained from the major component in the mixture: Expected mass for the AgrDI thiololactone=962.374 Da (961.9 mass). FIG. 1C. Reverse-phase HPLC of the crude AgrDII reaction mixture. Inset shows the ESMS of the major component in the mixture: expected mass for the AgrDII thiololactone=880.0129 Da (879.9 mass). Both HPLC spectra were obtained using a linear gradient of 0-73% buffer B over 30 minutes (buffer B=CH3CN:H2O: trifluoracetic acid; 90:10:1). ESMS was performed on a PE-Sciex API-100 single-quadrupole electrospray mass spectrometer. Calculated masses were obtained using the program MacProMass (Sunil Vemuri and Terry Lee, City of Hope, Duarte, Calif.).

FIGS. 2A-2C. Synthetic thiololactone peptides are biologically active. FIG. 2A and FIG. 2B show representative data for activation and inhibition, respectively, of the agr response by a synthetic thiololactone peptide. Degree of activation/inhibition of the agr response, based on β-lactamase activity (see Table 1), is shown as a plot of Vmax versus peptide concentration. FIG. 2A. Activation of the agr response in group II S. aureus cells by synthetic AgrDII. FIG. 2B. Inhibition of the agr response in group I S. aureus cells by synthetic AgrDII. FIG. 2C. Effect of replacing each residue within the AgrDII sequence with alanine on activation and inhibition activity.

FIG. 3A. Activation of the agr response occurs via an intra-class interaction in which a self AgrD peptide interacts with a self AgrC receptor. Specific AgrD/AgrC interactions lead to proper positioning of the peptide to undergo transacylation with a nucleophile within the receptor, leading to a signal-transducing conformational change. FIG. 3B. Inhibition of the agr response occurs via an inter-class, non-covalent interaction which serves exclude the strain's own activating peptide from the receptor. This interaction is also specific.

FIG. 4A. Bioluminescent activity of agr$^+$ (agr-I) bacteria carrying agrp$_3$-lux following subcutaneous injection in the flank region of SKH-1 mice. Signal intensity is indicated by a pseudocolor scale. Relative light units (RLU) per lesion were plotted as a function of time for an infecting dose of $10^8$ bacteria carrying either (FIG. 4B) agrp$_3$-lux or (FIG. 4C) blaZp-lux in agr$^+$ (filled circles) and agr$^-$ (open circles) backgrounds in groups of 3 mice. (FIG. 4D) Viable counts of agr$^+$ (filled triangles) and agr$^-$ (open triangles) bacteria were enumerated at different points during infection. (FIG. 4E) Activity of agrp$_3$-lux (filled circles) and blaZp-lux (filled diamonds) in agr$^+$ bacteria following infection of PMN depleted mice.

FIGS. 5A-D. Autoinduction of agr in vivo. FIG. 5A. The group-specific AIP-II biosensor strain responds in trans only to an agr-II strain producing its cognate autoinducer, AIP-II, on solid media. FIG. 5B. $10^8$ agr-I, agr⁻ (agr-II::tetM) or agr-II were mixed with equal numbers of the AIP-II biosensor and a subcutaneous infection was initiated (n=3) followed by in vivo imaging. The results with a single mouse represent the series. FIG. 5C. Bioluminescence generated from $5\times10^6$ agr-II carrying agrp$_3$-lux (filled squares) or blaZp-lux (filled triangles) as described in FIG. 1. FIG. 5D. At top are plotted blaZp-lux activities during infection with agr-II and its agr-null derivative. Below are shown the corresponding bacterial colonies obtained by plating identical serial dilutions of the homogenized tissue excised from the site of infection at 0 h, 3 h, and 6 h. Each panel shows the bacterial colonies from a single lesion.

FIG. 6A. Structure of the agr-II autoinducer AIP-II (SEQ ID NO: 1), an agr-I signaling antagonist. FIG. 6B. Determination of AIP-II half-life. The y-axis for the graph indicates the percent maximal activation of agrp$_3$-blaZ and the x-axis represents the concentration of AIP-II. The $EC_{50}$ in PBS was 56.1 nM, and in serum it was 134 nM, indicating that the AIP-II half-life in vivo is <4 h. FIG. 6C. The effect of AIP-II on $10^8$ agr-I bacteria carrying agrp3-lux (filled squares, untreated; open squares, AIP-II treated); FIG. 6D. blaZp-lux (filled triangles, untreated; open triangles, AIP-II treated); and FIG. 6E. The effect of AIP-II on bioluminescence of agr-I bacteria carrying blaZp-lux or agrp$_3$-lux when grown on solid media (24 h), on α-hemolysin production when grown on 5% sheep blood agar (24 h) and on lesion size in the murine subcutaneous model (at 96 h) in comparison with agr⁻.

FIGS. 7A-C. Histological comparison of lesions caused by agr⁺ (agr-I) cells and sterile supernatant. FIG. 7A. Exoproteins from agr⁺ and agr⁻ supernatants were precipitated with 10% trichloroacetic acid and separated by 10% Tricine SDS-PAGE. After staining with Coomassie brilliant blue and densitometry analysis several bands were identified that are differentially expressed between the two strains. Sterile culture filtrate was diluted up to 1:4 in PBS and 0.1 ml was injected without cytodex beads. FIG. 7B. Gross lesions at 48 h caused by agr⁺ cells, agr⁺ supernatant and agr⁻ supernatant. FIG. 7C. Histological sections of the lesions caused by agr⁺ cells and agr⁺ supernatant were stained with hematoxylin and eosin. A Gram stain indicated the dark stained regions of the lesion caused by agr⁺ cells represent clumped staphylococci (Sa). For comparison the inset boxes illustrate the integrity of the subcutaneous musculature (SM) (demarcated with dashed lines) and the epidermis (E) in a lesion caused by agr⁻ cells. The scale bar represents 200 µM.

DETAILED DESCRIPTION

The present invention provides a cyclic peptide comprising the structure:

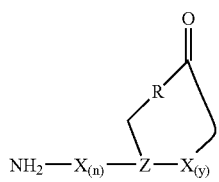

wherein X is selected from the group consisting of an amino acid, an amino acid analog, a peptidomimetic and a non-amide isostere, Z is selected from the group consisting of a synthetic amino acid and a biosynthetic amino acid, R is selected from the group consisting of oxygen, nitrogen, sulfur and carbon, n is 0 to 10 and y is 1 to 10.

The present invention also provides a cyclic peptide comprising the amino acid sequence of $NH_2$—$X_{(n)}$-Z-$X_{(y)}$—COOH and a cyclic bond between the Z residue and COOH other than a thioester bond, wherein X is selected from the group consisting of an amino acid, an amino acid analog, a peptidomimetic and a non-amide isostere, Z is selected from the group consisting of a synthetic amino acid and a biosynthetic amino acid, n is 0 to 10 and y is 1 to 10.

An embodiment of the present invention is a compound comprising the provided peptide, peptidomimetic thereof or polymer thereof.

A further embodiment of the invention extends to a method for the preparation of the present cyclic peptide, which method comprises assembling the linear constituents of the peptide under preparation on a PEGA resin support to form a protected and bound peptide chain; treating the resulting peptide chain to cause deprotection thereof; thereafter treating the deprotected peptide with buffer at a neutral pH for a period of time sufficient to cleave said peptide from said solid phase support and to form the cyclic peptide in object; and recovering the cyclic peptide. More particularly, the method comprises assembling the linear peptide chain corresponding in composition to the said cyclic peptide onto a solid phase resin support containing 3-mercapto-propionamide-polyethylene glycol-poly-($N_1N_4$-dimethacrylamide)(HS-PEGA) to form a protected assembled peptide; treating the protected assembled peptide of the previous step to deprotect the said assembled peptide; treating the deprotected peptide with aqueous buffer at a pH of about 7.0 for a period of time sufficient to form the said cyclic peptide and to cleave the peptide from the solid phase resin support; and recovering the cyclic peptide in object.

Figure 1A:
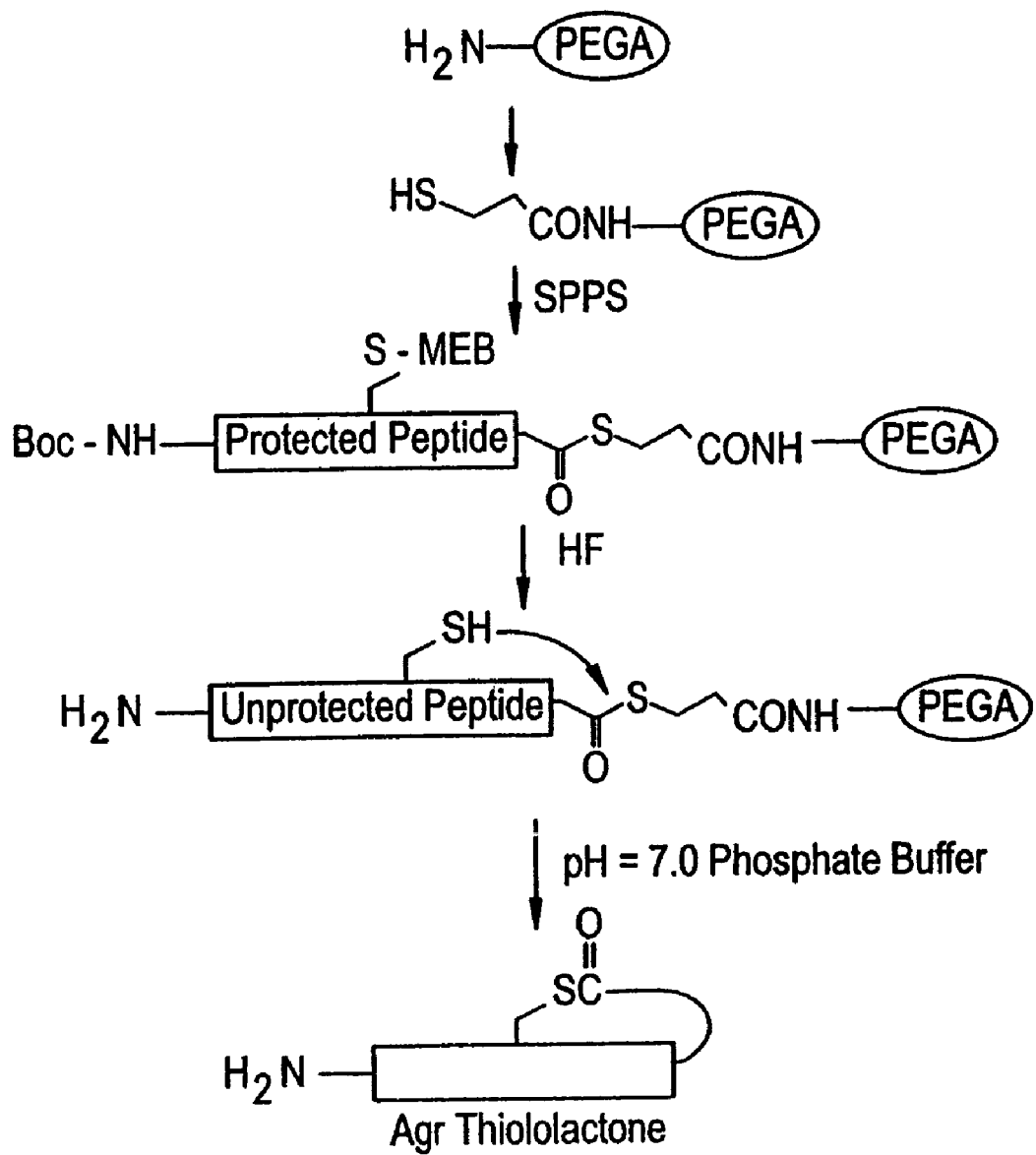
FIGS. 1A-1C. Chemical synthesis of AgrD autoinducing peptides.

As described in detail in Example 1 and as depicted in FIG. 1A herein, the present method utilizes a solid phase cyclization protocol as its last step in the formation of the inventive cyclic peptides. Also, the method involved the initial preparation of a fully unprotected peptide on a solid support through a reactive thiol ester bond. Accordingly, a representative solid phase resin support suitable for use in the present method may comprise BOC-AA-(linear assembled peptide)-PEGA. Further, the deprotection treatment that follows the assembly of the peptide on the resin support may for example, be performed with HF for a period of time of about 1 hour. Thereafter, the cleavage of the peptide from the support and the formation of the cyclic peptide may be performed with a buffer such as $Na_2PO_4$ and acetonitrile. Also, this step is performed for a period of time sufficient to achieve both cleavage and cyclization, which may for example, extend for a period of about 12 hours. Naturally the foregoing reagents and process parameters may vary within the scope of the invention, and the invention is intended to cover such variations within its spirit and scope.

In another embodiment of this invention, the cyclic peptide is capable of inhibiting agr response. In another embodiment of this invention, Z has a side chain comprising oxygen or nitrogen. In another embodiment of this invention, Z presents a functionality capable of cyclizing through a thioether group, an ether group or a carbon-carbon group. In yet another embodiment of this invention, the cyclic bond is a lactam or lactone bond. In still another embodiment, y is 4. According to yet another embodiment of this invention, the peptide has an amino acid sequence that comprises G-V-N-A-X-S-S-L-F (SEQ ID NO: 1), G-A-N-A-X-S-S-L-F (SEQ ID NO: 2), G-V-A-A-X-S-S-L-F (SEQ ID NO: 3), A-V-A-N-X-S-S-L-F (SEQ ID NO: 4), G-V-N-A-X-A-S-L-F (SEQ ID NO: 5), G-V-N-A-X-S-A-L-F (SEQ ID NO: 6), G-V-N-A-X-S-S-A-F (SEQ ID NO: 7), and X-S-S-L-F (SEQ ID NO: 8). Still, in yet another embodiment of the present invention, the peptide has an amino acid sequence that comprises a hydrophobic amino acid in the carboxy terminal or penultimate carboxyterminal position.

The present invention also provides a pharmaceutical composition comprising the described peptide and a pharmaceutically acceptable carrier. In an embodiment of this invention, the carrier is selected from the group consisting of a diluent, an aerosol, a topical carrier, an aqueous solution, a nonaqueous solution and a solid carrier.

Finally, the present invention provides a method for treating S. aureus infection in a subject comprising administering to the subject an amount of the provided pharmaceutical composition in an amount effective to treat the infection, wherein said treatment further comprises administering at least one antibiotic to said subject.

Staphylococcal Infections

Staphylococcal infections produce pus-filled pockets, or abscesses, that may be located just beneath the surface of the skin or deep within the body. A localized staphylococcal infection of the skin is generally confined to a ring of dead and dying white blood cells and bacteria. The majority of superficial skin abscesses eventually burst on their own, but some require medical intervention to drain the abscess (also known as a boil).

A small fraction of localized staphylococcal infections enter the bloodstream and spread throughout the body. In children, such systemic or disseminated infections frequently affect the ends of the long bones of the arms or legs, causing a bone infection called osteomyelitis. When adults develop invasive staphylococcal infections, bacteria are most apt to cause abscesses of the brain, heart, kidneys, liver, lungs, or spleen.

Diagnosis

Blood tests that reveal unusually high concentrations of white blood cells can suggest staphylococcal infection, but diagnosis is generally based on laboratory analysis of material removed from pus-filled sores, and on analysis of normally uninfected body fluids, such as, blood and urine. X-rays can enable a skilled practitioner to locate internal abscesses and estimate the severity of infection. Needle biopsy (removing tissue with a needle) and subsequent microscopic examination may be used to assess bone involvement.

Treatment

Severe or recurrent infections may be treated with a seven to ten day course of penicillin or other oral antibiotic. A skilled practitioner is able to determine which antibiotic or antibiotics to prescribe and the appropriate dosage, depending on the location of the infection, the age and condition of the patient, and the identity of the causal bacteria.

For more serious infections, antibiotics may be administered intravenously for as long as six to eight weeks. Intravenous (IV) antibiotics are also used to treat staphylococcal infections around the eyes or on other parts of the face.

Surgery may be required to drain or remove abscesses that form on internal organs, or on shunts or other devices implanted inside the body.

Antibiotic regimens used for the treatment of serious staphylococcal infections include, but are not limited to vancomycin, linezolid, and oxacillin. It is also understood that these and other known antibiotics are frequently used in combination. A list of some of the antibiotics of choice for the treatment of staphylococcal infections are indicated below, along with information relating to their mechanism of action and recommended doses.

Nafcillin (Nafcil, Unipen, Nallpen) may be used for initial therapy for potentially penicillin G-resistant streptococci or staphylococci infections. Parenteral therapy is used initially to treat severe infections, but oral therapy may be used once the condition has stabilized. Parenteral administration is generally curtailed at 1-2 days, due to the potential for thrombophlebitis, the development of which is particularly relevant in the elderly. A switch to oral administration is recommended, as clinically indicated, following parenteral administration. Recommended adult dose is 2 g IV q4h, whereas recommended pediatric dose is 100-200 mg/kg/d IV in 4 doses. To optimize therapy, it is critical to determine the causative organisms and establish their anti-microbial susceptibility. Greater than 10 days of treatment is recommended to eliminate infection and prevent sequelae (e.g., endocarditis, rheumatic fever). Eradication of disease can be evaluated by taking cultures after treatment to confirm absence of causative microbes.

Vancomycin (Vancocin, Vancoled) is indicated for patents who do not tolerate or have failed to respond to penicillins and cephalosporins or for those patients whose infections have suggested the presence of resistant staphylococci. Recommended adult dose is 1 g or 15 mg/kg IV q12h. Recommended pediatric dose is 30-40 mg/kg/d in 2 doses Cefazolin (Ancef, Kefzol) is a first-generation semi-synthetic cephalosporin that arrests bacterial cell wall synthesis, thereby inhibiting bacterial growth. It is primarily active against skin flora, including S. aureus and is typically used alone for skin and skin-structure coverage. IV and intramuscular (IM) dosing regimens are similar. Recommended adult dose is 1 g IV q8h. Recommended pediatric dose is 50-100 mg/kg/d IV in 3 s.

Clindamycin (Cleocin) is a lincosamide for treating serious skin and soft tissue staphyiococci infections. It is also effective against aerobic and anaerobic streptococci (except enterococci). It inhibits bacterial growth, possibly by blocking dissociation of peptidyl t-RNA from ribosomes, causing RNA-dependent protein synthesis to arrest. Recommended adult dose is 600 mg IV q8h; 150-300 mg per oral (PO) q8h. Recommended pediatric dose is 25-40 mg/kg/d PO/IV in 3 doses.

Dicloxacillin (Dycill, Dynapen) binds to one or more penicillin-binding proteins, which, in turn, inhibits synthesis of bacterial cell walls. It is used to treat infections caused by penicillinse-producing staphylococci. It may be used to initiate therapy when staphylococcal infection is suggested. Recommended adult dose is 500 mg PO q6h. Recommended pediatric dose is 25 mg/kg/d PO in 4 doses.

Trimethoprim-sulfamethoxazole (Bactrim, Bactrim DS, Septra, Septra DS) inhibits bacterial growth by inhibiting synthesis of dihydrofolic acid. Recommended adult dose is 160/800 mg PO q12h. Recommended pediatric dose (which is only applicable to children >2 years) is 6-12 mg of trimethoprim/kg/d in 2 doses.

Minocycline (Minocin) inhibits protein synthesis and thus bacterial growth by binding to 30S and possibly 50S ribosomal subunits of susceptible bacteria. Notably, it is active against methicillin-susceptible S. aureus (MSSA) and methicillin-resistant S. aureus (MRSA). Recommended adult dose is 100 mg PO/IV q12h. Recommended pediatric dose is 2-4 mg/kg/d PO divided in 2 doses.

Linezolid (Zyvox) prevents formation of functional 70S initiation complex, which is essential for bacterial translation. It is bacteriostatic against staphylococci. Recommended adult dose is 400-600 mg PO/IV q12h. A recommended pediatric dose has not been established.

Quinupristin/dalfopristin (Synercid), which belongs to the macrolide/lincosamide/streptogramin group of antibiotics, inhibits protein synthesis and is usually bacteriostatic. It is used most frequently for treating vancomycin-resistant enterococcal infections but is also an option for methicillin-resistant staphylococcal infections. Recommended adult dose is 7.5 mg/kg IV q8h. A recommended pediatric dose has not been established.

Cephalexin (Keflex, Biocef, Keftab) binds to penicillin-binding proteins, which, in turn, inhibits synthesis of bacterial cell walls. Resistance to this antibiotic generally arises following alteration of penicillin-binding proteins. It is effective for treating infections caused by streptococci or staphylococci, including penicillinase-producing staphylococci. It may be used to initiate therapy when streptococcal or staphylococcal infection is indicated. Recommended adult dose is 500-1000 mg PO q6h; not to exceed 4 g/d. Recommended pediatric dose is 25-50 mg/kg/d PO divided q6h; not to exceed 3 g/d.

A number of conditions or diseases are described herein and known in the art to be associated with sequestered, encapsulated, or localized S. aureus infections. Localized S. aureus infections include, but are not limited to, deep tissue abscesses, endocarditis, septic arthritis, and osteomyelitis. Following appropriate initial stages of treatment, which may call for drainage (for treatment of, e.g., deep tissue abscesses, septic arthritis, or osteomyelitis) and potentially lavage of the affected area to remove, in principle, all of the bacteria, the peptides and/or compositions of the invention are introduced directly into the affected treated area to address the potential complication of residual bacteria that may remain after initial stages of treatment. The peptides or compositions comprising same may also be administered intravenously under such circumstances, either alone or in combination with direct application of the peptides or compositions to pre-treated localized sites of sequestered infection. The peptides or compositions comprising same may be administered in conjunction with appropriate antibiotics, which may also be administered directly to the affected treated area and/or systemically (e.g., intravenously or orally) to the patient.

Deep Tissue Abscesses

Deep tissue abscesses present clinical challenges that, in general, are not relevant to superficial skin abscesses. Deep tissue abscesses frequently involve surgical intervention, when the abscess is accessible to such means and the benefits to the patient outweigh the risks involved. Surgical intervention involves drainage of the accumulated pus in the abscess, which may be achieved by aspiration of the infected material using a needle or the like. Under some circumstances, a shunt may be positioned to facilitate continued drainage following surgery.

The peptides and/or compositions of the present invention are then used advantageously to abrogate and/or prevent resurgence of any residual bacteria that may potentially remain after drainage. In brief, the peptides and/or compositions of the invention may be administered directly into the cavity of the abscess after routine drainage and appropriate lavage procedures. The peptides and/or compositions of the invention may be administered directly into the cavity of a drained abscess at a concentration, which may be determined by a skilled practitioner. Alternatively, or in addition to the local delivery of high concentrations of a peptide of the invention, the peptides of the invention may be administered intravenously. Moreover, the peptides or compositions comprising same may be administered in conjunction with appropriate antibiotics, which may also be administered directly to the affected treated area and/or systemically to the patient.

The utility of medical intervention involving direct delivery of the peptides and/or compositions of the invention into the cavity of a drained abscess is underscored by results presented in Example 4. As described therein, the peptides of the invention are used successfully to prevent maturation of an abscess, even in the presence of a large inoculum of S. aureus bacteria. In that the number of residual of S. aureus bacteria remaining in a properly drained abscess is a fraction of that used as an inoculum in Example 4 ($10^6$ to $10^8$ depending on the strain), administration of the peptides or compositions comprising these peptides should minimally delay, if not prevent development of a subsequent or recurrent staphylococcal lesion in a properly drained abscess.

Septic Arthritis

S. aureus is generally recognized as the principal cause of nongonococcal bacterial arthritis in humans. The role of the S. aureus agr system as a virulence determinant in the pathogenesis of septic arthritis has been examined (Abdelnour et al. (1993) Infect and Immun 61:3879-3885). As alluded to herein above, there are at least fifteen genes coding for potential virulence factors in S. aureus that are regulated by a putative multicomponent signal transduction system encoded by the agr/hld locus. Indeed, Agr and hld mutants exhibit decreased synthesis of extracellular toxins and enzymes (e.g., alpha-, beta-, and delta-hemolysin, leucocidin, lipase, hyaluronate lyase, and proteases) and increased synthesis of coagulase and protein A as compared to wild-type strains. Results generated using a murine model of S. aureus-induced arthritis have shown that the agr system of S. aureus is an important virulence determinant that affects the ability of the bacteria to home to the joints and create an inflammatory condition therein (Abdelnour et al. (1993) Infect and Immun 61:3879-3885). In that the cyclic peptides of the present invention inhibit the agr response, a response that clearly plays a significant role in the induction and progression of septic arthritis, these findings underscore the efficacious potential of the cyclic peptides of the present invention in the treatment of septic arthritis.

A diagnosis of septic arthritis is determined based on a variety of criteria, including patient symptoms and medical history, a complete physical exam, and analyses of synovial fluid and blood tests. In cases of suspected septic arthritis, a medical practitioner will usually perform an arthrocentesis, which is a procedure that involves withdrawing a sample of synovial fluid from the joint with a needle and syringe for testing. The fluid is tested for white blood cells, numbers of which are usually high in septic arthritis, and for bacteria and other organisms. Routine analyses of blood and urine specimens are also recommended to exclude the possibility of other causes and/or disorders that are associated with a combination of joint pain and fever. X-ray visualization of the joint may also be used to assess progression the disease and the extent of damage to the joint in question.

Following a positive diagnosis of septic arthritis, medical management of the condition focuses on adequate and timely drainage of the infected synovial fluid, administration of appropriate anti-microbial therapy, and immobilization of the joint to control pain.

Medical therapy involves administration of antibiotics to a patient afflicted with septic arthritis. At the outset of treatment, antibiotics are frequently administered intravenously to ensure that the infected joint receives sufficient medication to kill the bacteria expeditiously. The remaining course of antibiotics may be taken orally, at the discretion of the attending physician. In general, medical therapy involving parenteral antibiotics is continued for 3-4 weeks, but each case must be evaluated individually.

The peptides and compositions of the present invention may be used to advantage in conjunction with intravenous or oral antibiotics under circumstances wherein *S. aureus* is suspected or known to be a causative agent of septic arthritis. Following percutaneous drainage of the infected joint, the peptides and compositions of the invention may be administered directly into the drained joint and/or intravenously at a therapeutically effective dose to delay or prevent resurgent growth of any potential residual bacteria remaining in the joint. The peptides or compositions of the invention may also be used advantageously in conjunction with antibiotics that are delivered directly into a drained joint.

The method used for draining accumulated joint fluid (e.g., percutaneous or surgical) is determined by the attending physician. In general, needle aspiration is performed initially, and repeated joint taps may be performed at a frequency sufficient to prevent significant re-accumulation of fluid. Immediate surgical drainage is generally reserved for septic arthritis of the hip, due to the difficulties involved in accessing this joint for repeated fluid removal. For most other joints, surgical drainage is used only if medical therapy fails to alleviate symptoms in two to four days. If septic arthritis occurs in an artificial joint, antibiotic treatment may need to be followed by surgery to replace the joint. Surgical drainage is indicated when one or more of the following is observed: the appropriate choice of antibiotic and vigorous percutaneous drainage fails to clear the infection after 5-7 days, the infected joints are difficult to aspirate (e.g., hip), or adjacent soft tissue is infected. Under some circumstances, arthroscopic lavage may also be performed. Arthroscopic drainage is replacing open surgical drainage as a preferred method. Arthroscopic drainage facilitates visualization of the joint interior, which enables a surgeon to drain pus, debride, and lyse adhesions.

Successful treatment of an infected implanted joint generally requires appropriate antibiotic therapy combined with removal of the hardware. A two-stage approach involving: (1) removal of the prosthesis, followed by 6 weeks of antibiotic therapy and (2) replacement with a new joint, wherein methylmethacrylate cement impregnated with an anti-infective agent (e.g., gentamicin or tobramycin) is used, has proven the most effective. The use of impregnated methylmethacrylate cement facilitates antibiotic diffusion into the surrounding tissues. An intermediate method involving concomitant replacement of the joint and antibiotic therapy has also been used successfully. This method is particularly effective when used in conjunction with antibiotic-impregnated cement.

As indicated herein above, the cyclic peptides and compositions of the present invention may be used to advantage in conjunction with intravenous, oral, and/or locally delivered antibiotics under circumstances wherein *S. aureus* is suspected or known to be a causative agent of septic arthritis.

In embodiments wherein an affected joint is drained via any means (e.g., percutaneous, surgical, or arthroscopic), the cyclic peptides and compositions of the invention may be administered directly into the drained joint at a therapeutically effective dose to prevent resurgent growth of any potential residual bacteria remaining in the joint. Such medical intervention is analogous to that described in Example 4, whereby the cyclic peptides of the invention are used to prevent maturation of an abscess, even in the presence of a large inoculum of *S. aureus* bacteria. In that the number of residual of *S. aureus* bacteria remaining in a properly drained joint is a fraction of that used as an inoculum in Example 4 ($10^6$ to $10^8$ depending on the strain), administration of the peptides or compositions comprising these peptides should delay or prevent development of a characteristic staphylococcal lesion in the joint typified by large numbers of bacteria and accumulation of pus.

In embodiments wherein it is determined that systemic administration of the cyclic peptides and compositions of the invention would be beneficial to a patient, such systemic delivery may be effected either alone or in conjunction with localized delivery of the cyclic peptides and compositions of the invention. At the discretion of the attending physician, the cyclic peptides and compositions of the invention may be administered in addition to at least one antibiotic as described herein. Typically, systemic doses are selected based on the weight, age, and condition of a patient and may be adjusted in accordance with the patient's response to an initial therapeutic dose.

The cyclic peptides of the invention are administered at a dose effective for reducing bacterial load in the patient as determined using standard techniques. "Reducing bacterial load" may be construed to refer to a significant decrease in the signs and symptoms of disease related to bacterial infection. For example, but not by way of limitation, reducing or eliminating fever in a patient and/or inflammation at the site of infection would be considered a satisfactory therapeutic objective. In certain embodiments of the invention, a cyclic peptide may be administered to a human patient at a dose of about 2.5 mg/kg to about 500 mg/kg. In a particular embodiment, a cyclic peptide may be administered to a human patient at a dose of 2.5 mg/kg to 100 mg/kg. In a more particular embodiment, a cyclic peptide may be administered to a human patient at a dose of 5 mg/kg to 50 mg/kg. The dose may be administered at appropriate intervals, e.g. but not limited to, daily or several times daily, or once, twice, or three times a week. In another preferred, specific, non-limiting embodiment of the present invention, soft or hard gelatin capsules containing approximately 500 milligrams of the cyclic peptide are administered at approximately 30 mg/kg of body weight of an animal.

Endocarditis

Endocarditis is an inflammation of the lining of the heart, and/or the heart valves, caused by infection. Diagnostic blood cultures and sensitivity tests are used to determine the causative agent of the infection. Notably, *S. aureus* is a common cause of bacterial endocarditis in patients with prosthetic valves and in intravenous drug users. *S. aureus* is also the most common cause of acute bacterial endocarditis in patients with previously normal cardiac valves. In this clinical presentation, the organisms frequently seed the blood stream from localized staphylococcal infections such as abscesses, cellulitis and osteomyelitis.

In view of the serious nature of the condition, hospitalization is generally required for the purposes of administering intravenous antibiotics and to facilitate careful monitoring of the patient's condition. Long-term intravenous antibiotic therapy (typically 4 to 8 weeks) is required to eradicate the bacteria from the heart chambers and vegetations on the valves. The antibiotic regimen is selected to be the most effective for eradication of the etiological organism and the best tolerated in view of the age and drug compatibilities of a particular patient. Moreover, an appropriate cocktail of antibiotics may be determined to be a preferred regimen for treatment of endocarditis. At the discretion of an attending physician, a patient who has resumed a stable condition may, however, be switched to oral antibiotics.

With respect to bacterial endocarditis caused by *S. aureus*, the vast majority of *S. aureus* isolates are resistant to penicillin. The atypical patient with bacterial endocarditis caused by a penicillin-susceptible *S. aureus* can be treated with penicillin. For *S. aureus* organisms that are resistant to penicillin, however, a critical factor in determining appropriate antibiotic treatment relates to the sensitivity of the organism to methicillin. Nafcillin or oxacillin (Bactocill) should be administered (2 g intravenously every four hours) for four to six weeks to patients with bacterial endocarditis caused by MSSA. Gentamicin may also be added for the first three to five days of treatment to protect the infected valve from further damage and potentially decrease the duration of bacteremia, thereby reducing the risk of extracardiac infection.

Intravenous drug users with right-sided endocarditis caused by MSSA can be treated effectively with a two-week course of nafcillin or oxacillin and gentamicin. Patients with evidence of left-sided involvement, extracardiac infection, renal insufficiency, congestive heart failure or other hemodynamic compromise are not, however, eligible for this regimen. Intravenous drug users with uncomplicated right-sided staphylococcal bacterial endocarditis can also be treated effectively with four weeks of oral ciprofloxacin (Cipro) and rifampin (Rifadin). Injection drug users with left-sided involvement or any complications of right-sided endocarditis should be treated with at least four weeks of nafcillin or oxacillin.

Patients with prosthetic valve infection caused by MSSA should be treated with a combination of oxacillin or nafcillin and rifampin (300 mg orally every eight hours) for at least six weeks. In addition, gentamicin should be administered during the first two weeks of this course of therapy.

For patients allergic to penicillin, a first-generation cephalosporin (cefazolin [Ancef] 2 g intravenously every eight hours) or vancomycin should be used instead of nafcillin or oxacillin for the treatment of MSSA endocarditis. MRSA strains have, however, been identified with increasing frequency as a causative agent of bacterial endocarditis, particularly in patients with prosthetic valves, right-sided endocarditis secondary to intravenous drug use, and nosocomial endocarditis. These organisms are resistant to cephalosporins, as well as methicillin. Patients with native valve endocarditis due to MRSA should be treated with vancomycin for four to six weeks.

Prosthetic valve infection with MRSA is frequently fatal and should be treated with a combination of vancomycin, rifampin and gentamicin. If the organism is resistant to all aminoglycosides, a fluoroquinolone should be used in combination with vancomycin and rifampin.

Infective-endocarditis involving a prosthetic valve generally requires surgical intervention to achieve optimal efficacy. Indeed, more patients with *S. aureus* prosthetic-valve endocarditis survive with medical and surgical therapy than with medical therapy alone, suggesting that prosthetic-valve endocarditis due to *S. aureus* might be a sufficient indicator to merit a therapeutic approach that includes valve replacement surgery.

Complications resulting from endocarditis include: congestive heart failure, perivalvular abscesses, intracardiac fistulae (i.e., abnormal connections within the heart), and emboli (blood clots which can travel through the circulation and cause strokes or other problems related to obstructed blood vessels). All these complications usually require surgery, either to remove vegetations or abscesses, to repair the valves, or to replace them with prostheses.

As described herein, the peptides and compositions of the present invention may be used to advantage in conjunction with intravenous antibiotics when *S. aureus* is suspected or known to be a causative agent of endocarditis. In a particular embodiment, the peptides and compositions of the invention may be administered intravenously, and in conjunction with appropriately administered antibiotics, at a therapeutically effective dose to a patient suffering from endocarditis to reduce the number of bacteria and/or prevent growth of the bacterial population.

Osteomyelitis

Osteomyelitis is an infection of the bone and bone marrow that tends to be difficult to treat. It is a progressive condition that results in inflammatory destruction of the bone, bone necrosis, and new bone formation. Bacterial osteomyelitis causes substantial morbidity worldwide, despite advances in the field.

The therapeutic treatment of choice for osteomyelitis depends on the route by which bacteria gained access to the bone, bacterial virulence, local and systemic host immune factors, and patient age. While imaging studies and nonspecific blood tests may suggest a potential diagnosis, invasive techniques are generally required to identify causative pathogens. The selection of antibacterial regimen is largely determined by knowledge of the relative activities and pharmacokinetics of individual drugs, supported by data from animal models.

Effective therapeutic intervention often requires a combined medicinal and surgical approach. Recent improvements in microvascular and distraction osteogenesis techniques and the use of laser Doppler enable more complete surgical resection of infected material and minimize potential loss of function. Despite recent advances, aggressive medical and surgical therapy fails in many patients with osteomyelitis. Thus, more accurate diagnostic methods and improved means for assessing and monitoring therapeutic efficacy, and novel approaches to eradicate sequestered bacteria are needed.

Hematogenous osteomyelitis in children can usually be treated with antibiotic therapy alone. It is, however, essential that the causative pathogen be identified in order to select the optimal antibiotic therapy. Improper management of disease with inappropriate antibiotic(s) encourages disease extension, necrosis, and sequestra formation. Indeed, a bone biopsy for culture purposes is necessary unless the patient has positive blood cultures and radiographic findings consistent with osteomyelitis. After cultures are obtained, a broad spectrum antibiotic regimen is selected that covers the most likely causative agents.

Once the etiologic organism is established, the antibiotic regimen should be modified, if needed, based upon susceptibility patterns. The patient should be treated for four to six weeks with appropriate anti-microbial therapy, beginning at the initiation of therapy or following the last major debridement surgery. If the initial medical management fails and the patient is clinically compromised by a recurrent infection, medullary and/or soft tissue debridement is necessary in conjunction with another four to six week course of antibiotics.

Oral antibiotics can be used in pediatric hematogenous osteomyelitis. Such pediatric patients should, however, receive 7-14 days of intravenous antibiotics or continue to receive intravenous antibiotics until systemic improvement occurs (usually observed at 3-4 days) prior to changing to an oral regimen.

For methicillin sensitive strains of *S. aureus*, the first choice antibiotic therapy is Nafcillin or cloxacillin, whereas the second choice antibiotic therapy is Cefazolin. For methicillin resistant strains of *S. aureus*, the first choice antibiotic therapy is Vancomycin, whereas the second choice antibiotic therapy is Trimethoprim-sulfamethoxazole or minocycline plus rifampin.

Surgical therapy: Surgical management of contiguous focus osteomyelitis, for example, can be very demanding. The principles of treating any infection, which are well applied to the treatment of infection in bone, include: adequate drainage, extensive debridement of all necrotic tissue, obliteration of dead spaces, stabilization, adequate soft tissue coverage, and restoration of an effective blood supply.

The number and nature of the required surgical procedures increases with the severity of the infection. Surgical procedures can be divided into the following categories: Category 1: removal of necrotic tissue by extensive debridement; Category 2: obliteration of dead space with flaps, antibiotic beads, and/or bone grafts; Category 3: provision of soft tissue coverage of the bone; and Category 4: stabilization of bone by external fixation or open reduction and internal fixation.

Category 1: Debridement surgery is the foundation of osteomyelitis treatment. It is the most commonly performed procedure and may need to be repeated multiple times. The goal of debridement is to reach healthy, viable tissue, but even when all necrotic tissue has been adequately debrided, the remaining tissue bed must be viewed as contaminated with the causative organism. Debridement should be direct, atraumatic, and executed with reconstruction in mind. All dead or ischemic hard and soft tissue is excised unless a noncurative procedure has been chosen. Surgical excision of bone is carried down to uniform haversian or cancellous bleeding, known as the paprika sign.

Category 2: Adequate debridement may create a large bony defect or dead space. Appropriate management of dead space created by debridement surgery must be achieved to arrest the disease and maintain the integrity of skeletal components. The goal of dead space management is to replace dead bone and scar tissue with durable vascularized tissue, such as local tissue flaps or free flaps, which may be used to fill dead space. An alternative technique is to place cancellous bone grafts beneath local or transferred tissues where structural augmentation is necessary. Open cancellous grafts without soft tissue coverage may be used when a free tissue transfer is not possible and local tissue flaps are inadequate.

Complete primary or delayed primary wound closure should be performed whenever possible. Antibiotic-impregnated acrylic beads can be used to sterilize and temporarily maintain dead space. The beads are usually removed within two to four weeks and replaced with a cancellous bone graft. The antibiotics most commonly used in beads are vancomycin, tobramycin, and gentamicin. Local delivery of antibiotics (amikacin, clindamycin) into dead space can also be achieved with an implantable pump. As indicated herein, the peptides of the invention and compositions thereof may be introduced in conjunction with such antibiotic delivery and may be administered locally and/or systemically.

Category 3: Adequate coverage of the bone by soft tissue is necessary to arrest osteomyelitis. Most soft tissue defects are closed primarily, but small soft tissue defects may be covered with a split thickness skin graft. In the presence of a large soft tissue defect or an inadequate soft tissue envelope, local muscle flaps and free vascularized muscle flaps may be placed in a 1- or 2-stage procedure.

Local and free muscle flaps, when combined with antibiotics and surgical debridement of all nonviable osseous and soft tissue for chronic osteomyelitis, have a success rate ranging from 65-100%. Local muscle flaps and free vascularized muscle transfers improve the local environment by supplying blood vessels, which are critical for host defense, antibiotic delivery, and osseous and soft tissue healing.

Category 4: If movement is present at the site of infection, measures must be taken to achieve permanent stability of the skeletal unit. Stability can be achieved with plates, screws, rods, and/or an external fixator. One type of external fixation allows bone reconstruction of segmental defects and difficult infected nonunions. The Ilizarov external fixation method uses the theory of distraction histogenesis, in which bone is fractured in the metaphyseal region and slowly lengthened. The growth of new bone in the metaphyseal region pushes a segment of healthy bone into the defect left by surgery. The Ilizarov technique is used for difficult cases of osteomyelitis when stabilization and bone lengthening are necessary. It also can be used to compress nonunions and correct malunions and in a small group of patients for reconstruction of difficult deformities that result from osteomyelitis. This technique, however, is labor intensive and requires an extended period of treatment. It is also associated with pain and the potential for subsequent infection. Vascularized bone transfer is also useful for the treatment of infected segmental osseous defects of long bones that are more than three centimeters in length.

Local antibiotic delivery: Systems for local delivery of antibiotics into tissues have been used to overcome limited penetration of systemic agents into poorly vascularized bone, to avoid toxicity, and to minimize the need for long-term parenteral antibiotics. Such systems include closed suction-irrigation, plaster pellets, fibrin, collagen, and porous calcium hydroxyapatite. The greatest experience has been with antibiotic-loaded polymethyl methacrylate (PMMA) bone cement. Antibiotic-loaded cement is used for prosthetic joint fixation to maintain and sterilize dead space with antibiotic-impregnated beads during surgery for chronic osteomyelitis and to maintain extremity length during 2-stage revision arthroplasty for infection.

Aminoglycosides, penicillins, cephalosporins, and clindamycin elute most effectively, whereas vancomycin elutes much less well. Even for drugs that elute most effectively, only a fraction of antibiotic is released. Approximately 10% of gentamicin added to PMMA may be recovered from the urine two months following hip arthroplasty. Extremely high local concentrations are, however, achieved as measured in surgical drains. To avoid systemic toxicity in adults, it is suggested that no more than 17.5 g of aminoglycoside be added to PMMA beads.

For localized delivery of the peptides and/or compositions of the invention, such as those described herein above for the treatment of conditions associated with sequestered or encapsulated S. aureus infections (e.g., abscesses and septic arthritis), the peptides may be administered directly into the affected area following appropriate drainage and preparatory measures at a therapeutically effective dose sufficient to prevent resurgent growth of any potential residual bacteria. Medical intervention using the peptides and compositions of the invention for the treatment of osteomyelitis following appropriate initial treatment (e.g., drainage and debridement) is analogous to results presented herein. As shown in Example 4, for instance, peptides of the invention are successfully used to prevent maturation of an abscess, even in the presence of a large inoculum of S. aureus bacteria. In that the number of residual of S. aureus bacteria remaining in a properly drained and treated site diagnosed as osteolyelitis is a fraction of that used as an inoculum in Example 4 ($10^6$ to $10^8$ depending on the strain), administration of the peptides or compositions comprising these peptides should delay or prevent subsequent development of a characteristic staphylococcal lesion in the bone typified by large numbers of bacteria and accumulation of pus.

As indicated herein above, the peptides and compositions of the present invention may be used to advantage in conjunction with intravenous, oral, and/or locally delivered antibiotics under circumstances wherein *S. aureus* is suspected or known to be a causative agent of septic arthritis.

In embodiments wherein an affected joint is drained via any means (e.g., percutaneous, surgical, or arthroscopic), the peptides and compositions of the invention may be administered directly into the drained joint at a therapeutically effective dose to prevent resurgent growth of any potential residual bacteria remaining in the joint. Such medical intervention is analogous to that described in Example 4, whereby the peptides of the invention are used to prevent maturation of an abscess, even in the presence of a large inoculum of *S. aureus* bacteria. In that the number of residual of *S. aureus* bacteria remaining in a properly drained joint is a fraction of that used as an inoculum in Example 4 ($10^6$ to $10^8$ depending on the strain), administration of the peptides or compositions comprising these peptides should delay or prevent development of a characteristic staphylococcal lesion in the joint typified by large numbers of bacteria and accumulation of pus.

Pre-Treatment of Biomaterials Prior to Implantation

The most common mode of bacterial growth in nature is within a biofilm, which consists of multiple layers of bacteria contained within a protective glycocalyx. Growth within a biofilm is particularly problematic with respect to musculoskeletal infections because staphylococci can form a biofilm in both native tissues and on the surface of implanted biomaterials (e.g., orthopedic implants). Biofilm-encased bacteria also exhibit an enhanced resistance to anti-microbial agents, due in part to their privileged/isolated locale, which makes biofilm-associated infections challenging to treat. The resolution of staphylococcal musculoskeletal infections often, therefore, requires surgical intervention to debride the infected tissue and/or remove the infected device.

The prevention of such complications is, therefore, an objective of some importance. It is, indeed, an objective of the present invention to use the cyclic peptides of the invention or compositions thereof to pre-treat biomaterials intended for subsequent implantation and thereby delay or prevent subsequent bacterial growth that can lead to biofilm formation. A pre-treatment step may be performed at the discretion of the attending physician, and may involve an application of the cyclic peptides of the invention or compositions thereof onto the implant by any reasonable means immediately prior to implantation. The cyclic peptides or compositions thereof may be administered alone or in conjunction with a suitable antibiotic(s). Such administration is anticipated to impair bacterial growth and, therefore, biofilm formation, thereby reducing the frequency of orthopedic infections.

As used herein, "pharmaceutically acceptable" refers to molecular entities and compositions that are physiologically tolerable and do not typically produce an allergic or similar untoward reaction, such as gastric upset, dizziness and the like, when administered to a human. A pharmaceutically acceptable carrier encompasses any of the standard pharmaceutically accepted carriers, such as phosphate buffered saline solution, water emulsions such as an oil/water emulsion or a triglyceride emulsion, various types of wetting agents, tablets, coated tablets and capsules. Typically such carriers contain excipients such as starch, milk, sugar, certain types of clay, gelatin, stearic acid, talc, vegetable fats or oils, gums, glycols, or other known excipients. Such carriers may also include flavor and color additives or other ingredients. The invention also provides for pharmaceutical compositions capable of inhibiting *S. aureus* infection together with suitable diluents, preservatives, solubilizers, emulsifiers and adjuvants. Other embodiments of the compositions of the invention incorporate particulate forms, protective coatings, protease inhibitors or permeation enhancers for various routes of administration, including but not limited to intravenous, intramuscular, parenteral, pulmonary, nasal and oral.

As used herein, an "effective amount" is the amount required to achieve a clinically significant reduction in *S. aureus* infection, preferably of at least 30 percent, more preferably of at least 50 percent, most preferably of at least 90 percent. Accordingly, the effective amount will vary with the subject being treated, as well as the condition to be treated. For the purposes of this invention, the methods of administration are to include, but are not limited to administration cutaneously, subcutaneously, intravenously, parenterally, orally, topically, or by aerosol.

As used herein, a "site of localized infection" refers to a region of tissue adversely affected by a bacterial infection (e.g., an *S. aureus* infection). Such sites are typically filled with bacteria, pus, and immune cells. Exemplary sites of localized infection include, but are not limited to: abscesses (e.g., superficial and deep tissue), regions of bone affected by osteomyelitis, regions of the heart affected by endocarditis, and joints affected by septic arthritis.

As used herein, a "treated site" refers to a former site of localized infection that has been drained of bacteria, pus, and immune cells. As indicated herein above, drainage may be achieved by any appropriate means (e.g., percutaneous, surgical, or arthroscopic). Drainage procedures are ideally directed to complete removal of bacteria, pus, and immune cells from the site, but it is understood that some residual evidence of the localized infection (such as, for example, dramatically reduced numbers of bacteria) may remain after drainage. As appropriate to the localized infection being drained, drainage may be followed by debridement and/or lavage. The term debridement (a standard term recognized in by medical practitioners) refers to surgical removal of torn, contaminated, or devitalized tissue. Lavage is a standard term in the art used to mean washing out of an organ or cavity. Such procedures are described herein and clinical circumstances under which these procedures are recommended are understood by skilled practitioners.

The present invention further contemplates therapeutic compositions useful in practicing the therapeutic methods of this invention. A subject therapeutic composition includes, in admixture, a pharmaceutically acceptable excipient (carrier) and one or more of a polypeptide analog or fragment of the provided peptide or peptide composition, or a peptidomimetic composition thereof as described herein as an active ingredient. The present invention further contemplates a therapeutic composition that includes, in admixture, at least one antibiotic in addition to a pharmaceutically acceptable excipient (carrier) and one or more of a polypeptide analog or fragment of the provided peptide or peptide composition, or a peptidomimetic composition thereof. A cocktail of the provided pharmaceutical composition in various combinations is also contemplated.

The preparation of therapeutic compositions which contain polypeptides or analogs as active ingredients (either alone or in combination with antibiotics) is well understood in the art. Typically, such compositions are prepared as injectables, either as liquid solutions or suspensions, however, solid forms suitable for solution in, or suspension in, liquid prior to injection can also be prepared. The preparation can also be emulsified. The active therapeutic ingredient is often mixed with excipients which are pharmaceutically acceptable and compatible with the active ingredient. Suitable excipients are, for example, water, saline, dextrose, glycerol, ethanol, or the like and combinations thereof. In addition, if desired, the composition can contain minor amounts of auxiliary substances such as wetting or emulsifying agents, pH buffering agents which enhance the effectiveness of the active ingredient.

A polypeptide or analog can be formulated into the therapeutic composition (either alone or in combination with antibiotics) as neutralized pharmaceutically acceptable salt forms. Pharmaceutically acceptable salts include the acid addition salts (formed with the free amino groups of the polypeptide or antibody molecule) and which are formed with inorganic acids such as, for example, hydrochloric or phosphoric acids, or such organic acids as acetic, oxalic, tartaric, mandelic, and the like. Salts formed from the free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

The therapeutic polypeptide- or analog-containing compositions (either alone or in combination with antibiotics) are conventionally administered intravenously, as by injection of a unit dose, for example. The term "unit dose" when used in reference to a therapeutic composition of the present invention refers to physically discrete units suitable as unitary dosage for humans, each unit containing a predetermined quantity of active material calculated to produce the desired therapeutic effect in association with the required diluent; i.e., carrier, or vehicle.

The compositions are administered in a manner compatible with the dosage formulation, and in a therapeutically effective amount. The quantity to be administered depends on the subject to be treated, capacity of the subject's immune system to utilize the active ingredient, and degree of inhibition desired. Precise amounts of active ingredient required to be administered depend on the judgment of the practitioner and are peculiar to each individual. However, suitable dosages may range from about 0.1 to 20, preferably about 0.5 to about 10, and more preferably one to several, milligrams of active ingredient per kilogram body weight of individual per day and depend on the route of administration. Suitable regimes for initial administration and booster shots are also variable, but are typified by an initial administration followed by repeated doses at one or more hour intervals by a subsequent injection or other administration. Alternatively, continuous intravenous infusion sufficient to maintain concentrations of ten nanomolar to ten micromolar in the blood are contemplated.

For localized treatment, a peptide of the invention is administered in a dose range of 0.1 to 500 μg. In a particular embodiment, a peptide of the invention is administered directly into a treated site of localized infection at a dose of 0.1 to 500 μg. In a more particular embodiment, a peptide of the invention is administered directly into a treated site of localized infection at a dose of 5 to 100 μg. As described herein, 10 μg of AIP-II in 5% DMSO in PBS was used for agr inhibition studies in mice. In view of the Examples set forth herein, a skilled practitioner would readily appreciate localized dosing parameters for an abscess, for example, based on the size of the infected area, severity of infection, and the size of the surrounding penumbra if one is apparent.

As used herein, "pM" means picomolar, "nM" means nanmolar, "uM, means micromolar, "mM" means millimolar, "ul" or "μl" mean microliter, "ml" means milliliter, "l" means liter.

As used herein, the term "synthetic amino acid" means an amino acid which is chemically synthesized and is not one of the 20 amino acids naturally occurring in nature.

As used herein, the term "biosynthetic amino acid" means an amino acid found in nature other than the 20 amino acids commonly described and understood in the art as "natural amino acids." Examples of "non-amide isosteres" include but are not limited to secondary amine, ketone, carbon-carbon, thioether, and ether moieties.

As used herein, the term "non-natural peptide analog" means a variant peptide comprising a synthetic amino acid.

As used herein, amino acid residues are preferred to be in the "L" isomeric form. However, residues in the "D" isomeric form can be substituted for any L-amino acid residue, as long as the desired functional property of immunoglobulin-binding is retained by the polypeptide. $NH_2$ refers to the free amino group present at the amino terminus of a polypeptide. COOH refers to the free carboxy group present at the carboxy terminus of a polypeptide. Abbreviations for amino acid residues are used in keeping with standard polypeptide nomenclature delineated in *J. Biol. Chem.*, 243:3552-59 (1969).

It should be noted that all amino-acid residue sequences are represented herein by formulae whose left and right orientation is in the conventional direction of amino-terminus to carboxy-terminus. Furthermore, it should be noted that a dash at the beginning or end of an amino acid residue sequence indicates a peptide bond to a further sequence of one or more amino-acid residues.

Amino acids with nonpolar R groups include: Alanine, Valine, Leucine, Isoleucine, Proline, Phenylalanine, Tryptophan and Methionine. Amino acids with uncharged polar R groups include: Glycine, Serine, Threonine, Cysteine, Tyrosine, Asparagine and Glutamine. Amino acids with charged polar R groups (negatively charged at pH 6.0) include: Aspartic acid and Glutamic acid. Basic amino acids (positively charged at pH 6.0) include: Lysine, Arginine and Histidine (at pH 6.0). Amino acids with phenyl groups include: Phenylalanine, Tryptophan and Tyrosine. Particularly preferred substitutions are: Lys for Arg and vice versa such that a positive charge may be maintained; Glu for Asp and vice versa such that a negative charge may be maintained; Ser for Thr such that a free —OH can be maintained; and Gln for Asn such that a free $NH_2$ can be maintained. Amino acids can be in the "D" or "L" configuration. Use of peptidomimetics may involve the incorporation of a non-amino acid residue with non-amide linkages at a given position.

Amino acid substitutions may also be introduced to substitute an amino acid with a particularly preferable property. For example, a Cys may be introduced as a potential site for disulfide bridges with another Cys. A His may be introduced as a particularly "catalytic" site (i.e., His can act as an acid or base and is the most common amino acid in biochemical catalysis). Pro may be introduced because of its particularly planar structure, which induces β-turns in the protein's structure.

The following examples are presented in order to more fully illustrate the preferred embodiments of the invention. They should in no way be construed, however, as limiting the broad scope of the invention. While the invention is described and illustrated herein by references to various specific material, procedures and examples, it is understood that the invention is not restricted to the particular material combinations of material, and procedures selected for that purpose. Numerous

EXAMPLES

Example 1

**Synthesis of a Novel Class of Peptides Responsible for *S. aureus* Bacterial Interference**

The initial synthetic route to the AgrD thiololactone peptides, involving the solution-based cyclization of a thiol ester precursor, proved problematic due to the difficulties associated with the synthesis of the linear starting material. A more efficient strategy was thus developed which involved solid-phase cyclization as the final synthetic step (FIG. 1A). Key to this process was the ability to prepare a fully unprotected peptide immobilized on solid-support through a reactive thiol ester bond. This was achieved using the recently described 3-mercaptopropionamide-polyethylene glycol-poly-(N,N-dimethylacrylamide) [HS-PEGA] support (Camarero et al. (1998) *J. Peptide Res.* 51:303-316) in combination with Boc-solid phase peptide synthesis (SPPS) (Schnolzer et al. (1992) *Int. J. Pept. Protein Res.* 40:180-193). The acid stability of the alkyl-thiol ester linkage between the peptide and the resin means that the completed peptide can be globally deprotected without being cleaved from the support. Generation of the desired thiololactone-peptide is then achieved by simply swelling the peptide-resin beads in aqueous buffer at pH 7.0, resulting in a chemoselective intramolecular cyclization/cleavage reaction. Note that this final step is made possible due to the excellent swelling properties of the PEGA support in water (Mendal (1992) *Tetrahedron Lett.* 33:3077-3080).

Figure 1B:
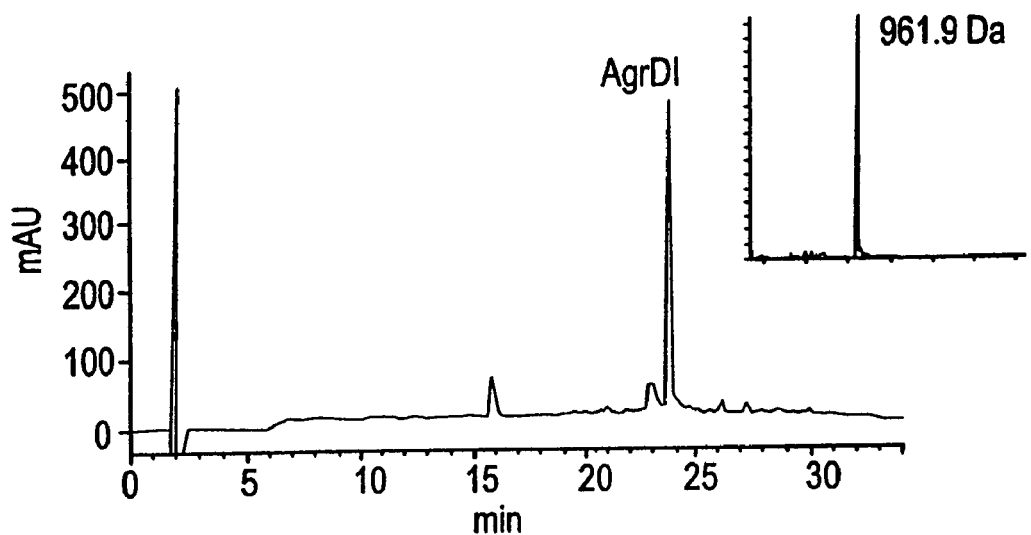
Figure 1C:
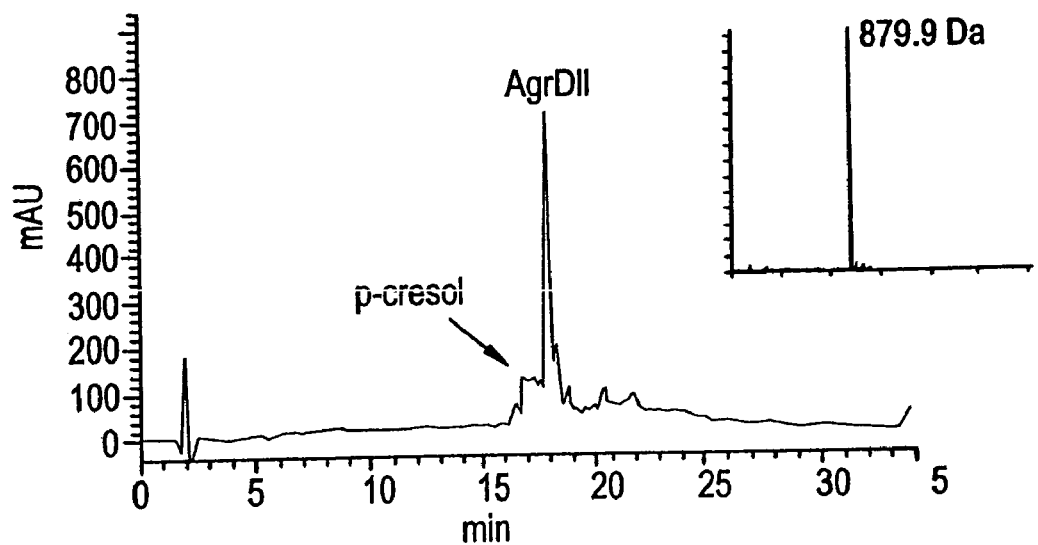

The synthetic approach illustrated in FIG. 1A was used to prepare peptides AgrDI and AgrDII from *S. aureus* group I and group II strains, respectively (The amino acid sequence of the group III AgrD peptide has not yet been established at the time of the present invention). In each case, the final cyclization/cleavage reaction was found to be remarkably clean giving rise to a single major component in excellent yield (FIG. 1B). Following purification, the ligation products were characterized as being the expected thiololactone-peptides by electrospray mass spectrometry, chemical reactivity to neutral hydroxylamine (Chou et al. (1952) *J. Biol. Chem.* 196:89) and two-dimensional $^1$H nuclear magnetic resonance (NMR) spectroscopy (Bax et al. (1985) *J. Magn. Reson.* 655:355-360; Wuthrich, *NMR of Proteins and Nucleic Acids* (Wiley, New York, 1986). (Peptide thiol esters react rapidly with neutral hydroxylamine to give the corresponding hydroxamate derivatives).

Figure 2A:
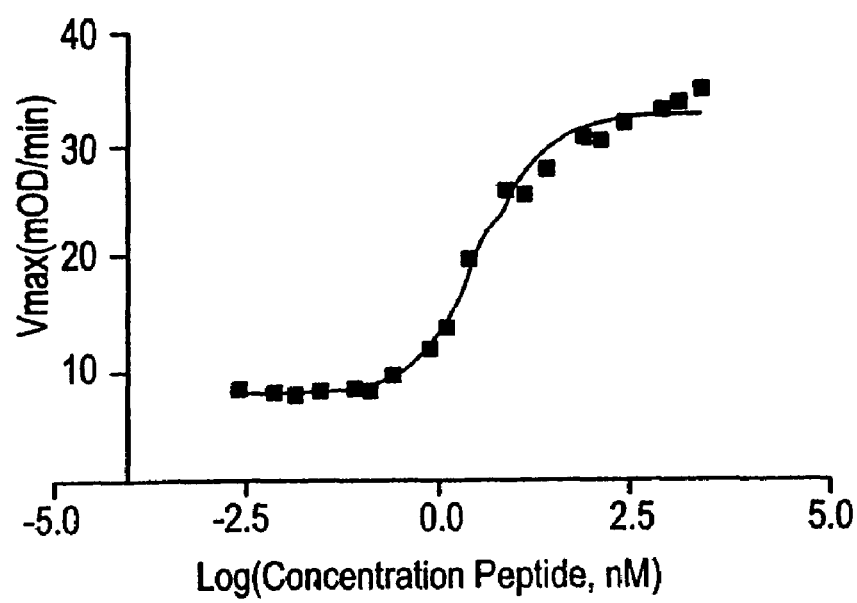
Figure 2B:
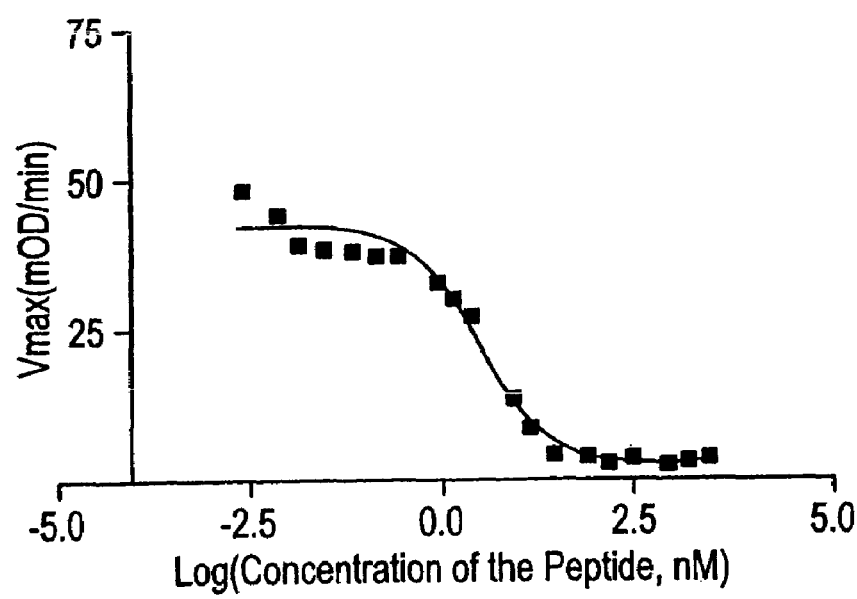

The biological activity of the synthetic AgrDI and AgrDII peptides was assayed using cultured *S. aureus* strains containing a β-lactamase reporter gene fused to the agrP3 promoter (Novick et al. (1995) supra). This allowed activation or inhibition of the agr response to be monitored spectrophotometrically using a colorimetric β-lactamase activity assay (Table 1). As with their naturally derived counterparts, synthetic AgrDI and AgrDII were found to activate the agr response only within their own *S. aureus* class, and inhibit the agr response only in *S. aureus* strains from the other two classes (Table 1). Further studies revealed a dose-dependent relationship between the amount of peptide added to the culture supernatant and the degree of activation/inhibition of the agr response (FIGS. 2A-2B). Analysis of the resulting sigmoidal response curves indicated that the ED50 and IC50 values, for activation and inhibition the agr response respectively, were in the low nanomolar range (Table 1). Moreover, these data indicate that there is a critical threshold concentration of the AgrD peptide required for activation of the agr response. This is consistent with the density-sensing/autoinduction mechanism previously proposed (Ji et al. (1997) supra). Importantly, no activation/inhibition activity was detected with linear carboxylate synthetic peptides corresponding to the AgrDI and AgrDII sequences, even at high μM concentrations (Table 1). That biological activity is restricted to the thiololactone-peptides, serves to confirm that this unusual posttranslational modification is present within the secreted AgrD peptides. The synthetic AgrD peptides shown in Table 1 include the following: Agr D1 Thiolactone. YSTCDFIM (SEQ ID NO: 9): Agr D2 Thiolactone, GVNACSSLF (SEQ IID NO: 1): Agr D2 Linear Thioester, GVNAASSLF (SEQ ID NO: 1): Agr D2 Linear Free Acid GVNASSSLF (SEQ ID NO: 1); Agr D2 Lactone, GVNASSSLF (SEQ ID NO: 1); and Agr D2 Lactam, GVNAXSSLF (SEQ ID NO: 1).

TABLE 1

BIOLOGICAL ACTIVITY OF SYNTHETIC AgrD PEPTIDES

| PEPTIDE | $ED_{50}$ Activation (nM) *S. aureus* Group | | | $IC_{50}$ Inhibition (nM) *S. aureus* Group | | |
|---|---|---|---|---|---|---|
| | I | II | III | I | II | III |
| Agr D1 Thiolactone YSTCDFIM (cyclic thiolactone structure) | 10.2 | No Activation | No Activation | No Inhibition | 2.9 | 3.2 |
| Agr D2 Thiolactone GVNACSSLF (cyclic thiolactone structure) | No Activation | 3.6 | No Activation | 3.4 | No Inhibition | 3.1 |

TABLE 1-continued

BIOLOGICAL ACTIVITY OF SYNTHETIC AgrD PEPTIDES

| PEPTIDE | $ED_{50}$ Activation (nM) S. aureus Group | | | $IC_{50}$ Inhibition (nM) S. aureus Group | | |
|---|---|---|---|---|---|---|
| | I | II | III | I | II | III |
| Agr D2 Linear Thioester 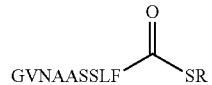 | No Activation | No Activation | No Activation | No Inhibition | No Inhibition | No Inhibition |
| Agr D2 Linear Free Acid 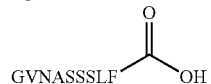 | No Activation | No Activation | No Activation | No Inhibition | No Inhibition | No Inhibition |
| Agr D2 Lactone 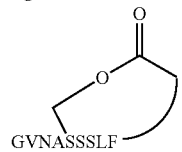 | No Activation | No Activation | No Activation | 7.9 | No Inhibition | n/d |
| Agr D2 Lactam 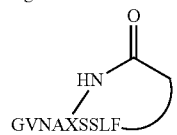 | No Activation | No Activation | No Activation | 0.21 | No Inhibition | n/d |

Example 2

Functional Significance of the Cyclic Ring Structure

The precision and convenience of the synthetic approach makes it possible to systematically vary the chemical structure of the peptides, thus enabling detailed structure-activity studies to be performed. With respect to the AgrD peptides, the initial focus was on the following questions: (i) Which amino acids within the sequence are most important for affinity/selectivity? (ii) What is the role of the thiololactone unit in activation and inhibition of the agr response? To address the first of these issues, an alanine scan was performed on the group II AgrD peptide. Each of the alanine-modified AgrDII peptide variants was prepared and characterized as before, and in each case the purified peptide assayed for its ability to activate or inhibit the agr response in each of the three S. aureus strains. Analysis of the results summarized in FIG. 2C, reveals that there are certain amino acids, residing both within the ring and the tail of the molecules, which are critical for the activation of the agr response (Asn-3, Leu-8, Phe-9). The alanine mutant peptides exhibit a wide activation profile, showing both increases and decreases in activity. In contrast, inhibition of the agr response appears to depend on amino acids only in the ring (Leu-8, Phe-9) and all of the inhibitory alanine-modified AgrDII peptides exhibit increased activity as compared to the wildtype.

The functional significance of the thiololactone structure in the AgrD peptides was investigated through the synthesis of a series of AgrDII variants (Table 1). To address whether a cyclic thiol ester group is strictly required for activity in the native peptide, a linear thiol ester analogue of AgrDII was prepared and assayed (see, Experimental Procedures for details). As with the linear carboxylate AgrDII variant described earlier, the linear thiol ester peptide was unable to either activate or inhibit the agr response even when added to cultured cells at μM concentrations. This result suggests that the cyclic structure present within the AgrD peptides is indispensable for biological activity.

Example 3

Lactone and Lactam Variants in the Cyclic Ring Structure Provide Peptides Capable of Inhibitory Activity without Activation Activity Thiol ester groups are moderately good acylating agents, a property which is utilized in several biological processes (Law et al. (1997) *Protein Science* 6:263-274; Xu et al. (1996) *EMBO J.* 15:5146-5153; Porter et al. (1996) *Science* 274: 255-259). It is intriguing to speculate that upon receptor binding, the thiololactone present in the AgrD peptides serves as an acyl donor for the covalent modification of a specific residue within AgrC. The effect of replacing the thiololactone unit in AgrDII with both ester (lactone) and amide (lactam) moieties (lactam) was of interest. In principle, both of these variants should be significantly less reactive than the thioester peptide, while the lactone variant of AgrDII should also be isosteric to wildtype. Synthesis of the desired AgrDII lactone and lactam variants was achieved via solution cyclization of a partially protected intermediate, followed by global side-chain deprotection. In particular, thiol esters are significantly more reactive towards nitrogen nucleophiles than oxygen esters (Bruice et al. in *Bioorganic Mechanisms* 1:259-297 (Benjamin, N.Y., 1966). As with the linear peptides described above, both the purified lactone and lactam variants were unable to activate the agr response in any of the three *S. aureus* strains (Table 1). However, both variants are able to inhibit the agr response in groups I and III *S. aureus* strains. Clearly, the reactive thioester bond is necessary for the activation of the agr response in vivo, however it is not necessary for inhibition.

Analysis of the biological properties of the various AgrDII peptide variants prepared in this study reveals the following: (i) Activation of the agr response is extremely sensitive to both the amino acid sequence and the chemical/stereochemical nature of the AgrD peptide; (ii) Inhibition of the agr response is sensitive to the backbone stereochemistry and the amino acid sequence of the AgrD peptide, but is not affected by changes in the chemical reactivity of the cyclic linkage. These observations suggest that activation and inhibition of the agr response occur through two different mechanisms.

The synthesis of virulence factors and other extracellular proteins responsible for pathogenicity in *Staphylococcus aureus* is under the control of the agr locus. A secreted agr-encoded peptide, AgrD, is known to be an effector of self-strain activation and cross-strain inhibition of this agr response. Preliminary analysis of AgrD peptides isolated from culture supernatants, suggested that they contain an unusual thiol ester-linked cyclic structure. In the present invention, chemical synthesis confirms that these AgrD peptides contain a thiololactone unit, and that this structure is absolutely necessary for full biological activity in the native peptides. Structure-function studies provided by the present invention identify and elucidate key aspects of the peptide structure involved in the differential activation and inhibition functions of the peptides. Novel, non-natural peptide variants are also provided which exhibit no activation activity while retaining (or enhancing) inhibitory activity. Peptides having such properties are useful for treating *S. aureus* infections.

Discussion

Figure 3A:
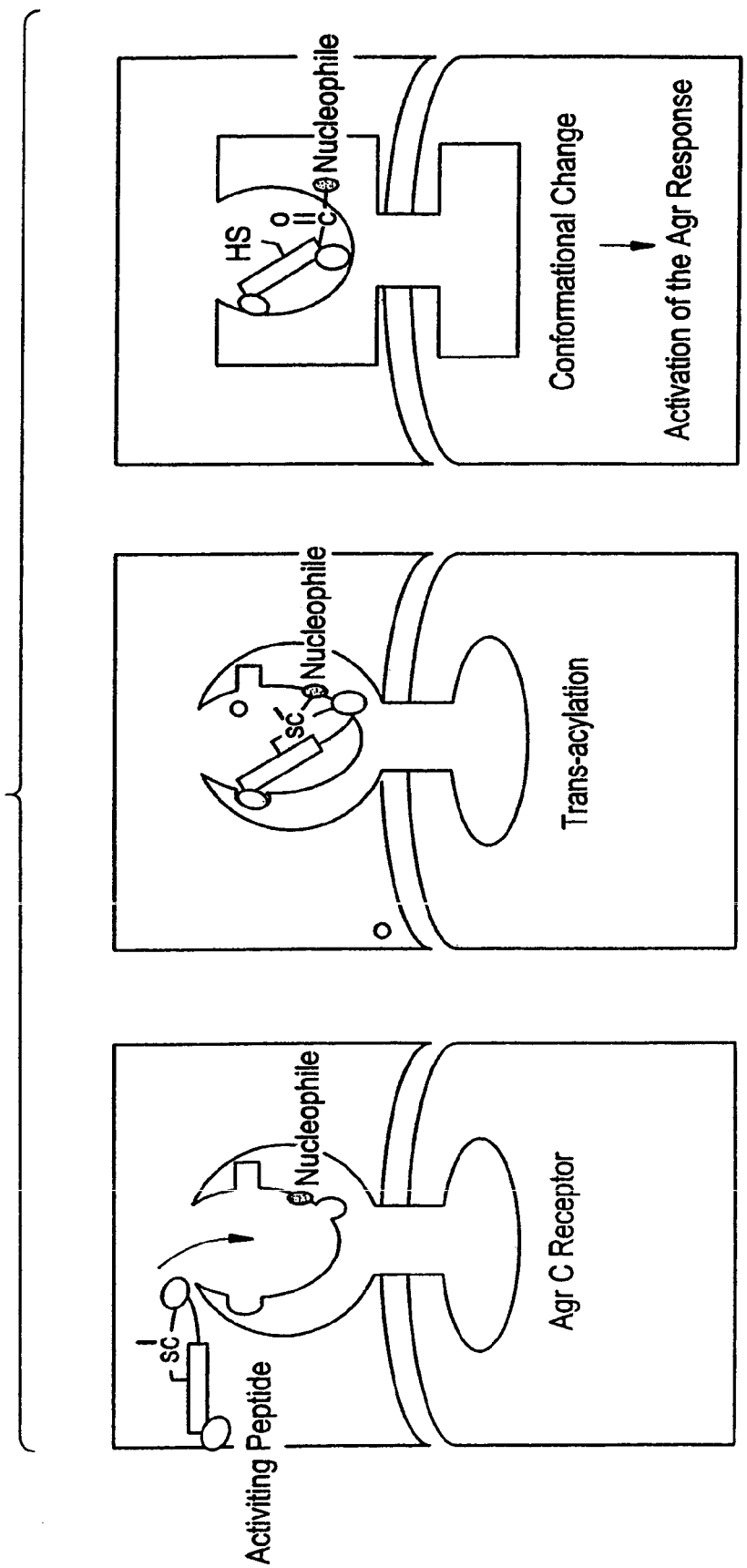
FIGS. 3A-B. Proposed model for the activation and the inhibition of the agr response.
Figure 3B:
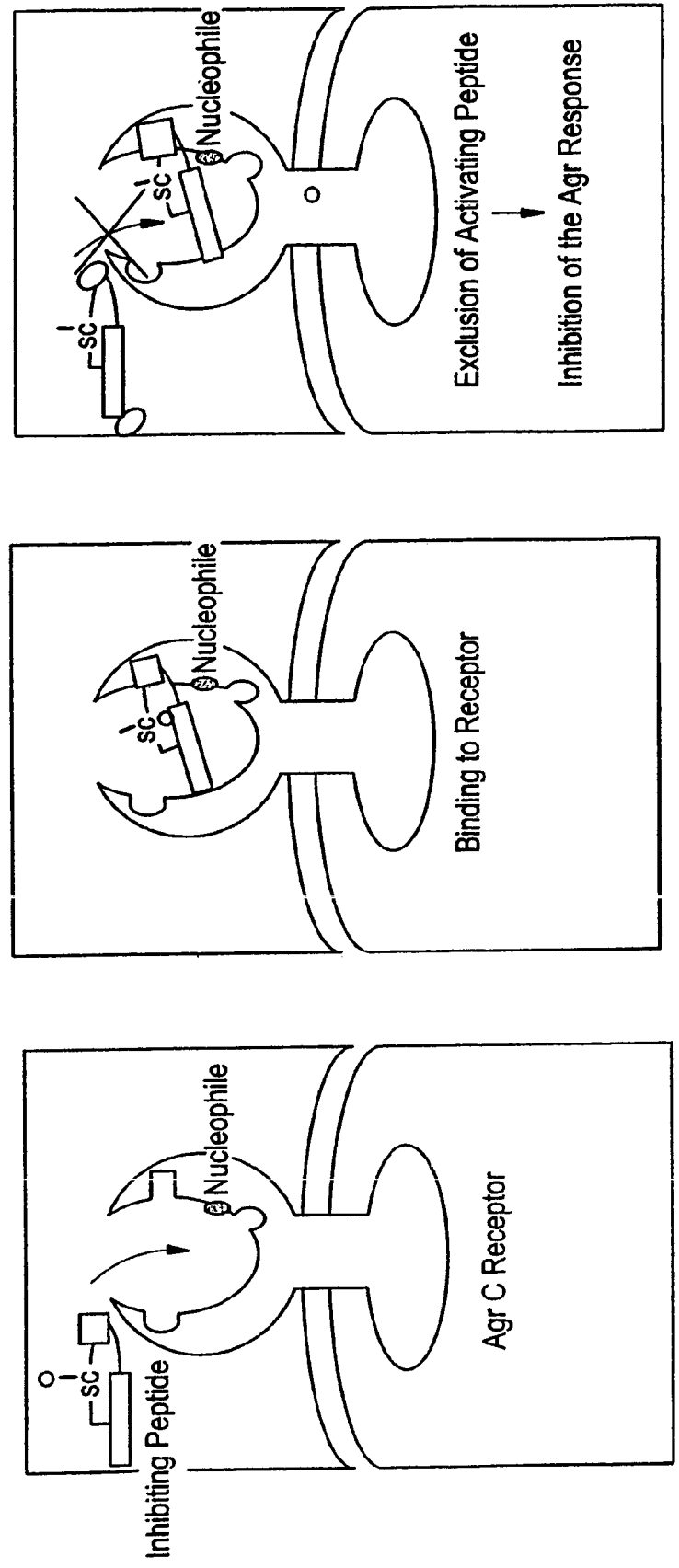

One proposed model in which an AgrD peptide binds its own AgrC receptor (i.e. from the same *S. aureus* class) in a different manner as compared to an AgrC receptor from another class is illustrated in FIG. 3. This may involve two slightly different orientations of the peptide within the receptor binding pocket, although more than one discrete binding site within the AgrC receptor cannot be excluded. It is further hypothesized that in the intra-class association, highly specific side-chain interactions between AgrC and AgrD result in the thiol ester linkage of the peptide being positioned adjacent to a nucleophilic group within the receptor. This juxtaposition leads to a trans-acylation reaction and activation of the agr response through an associated conformation change in the receptor. The thiol ester linkage is a sufficiently reactive moiety to participate in this trans-acylation step and would explain its presence within the AgrD peptide rather than one of the more common strategies for stereochemical restraint such as a disulfide- or amide-bond formation.

In contrast, no such juxtaposition would be present in the interclass receptor-ligand interaction due to the absence of these specific interactions. Thus the inhibition of the agr response would not involve a signal-transducing trans-activation step, but rather a non-covalent binding interaction which would serve to exclude the strain's own autoinducing AgrD peptide from the receptor binding pocket. This non-covalent binding interaction does require specific residues, as demonstrated in the alanine-scanning mutagenesis results. It is pertinent to note that the lactone and lactam variants, while being able to inhibit in the appropriate inter-class fashion, do not inhibit self. Inhibition by default, therefore, does not occur when a strain's own autoinducing lactone/lactam variant encounters its own receptor. This evidence further supports the proposed model in which activation and inhibition occur through discrete mechanisms.

In summary, chemical synthesis has been used to confirm the presence of a thiololactone structure within secreted AgrD autoinducing peptides. This highly unusual post-translational modification appears to be mandatory for full biological activity. Based on initial structure-activity studies, it is argued that the thiol ester functionality undergoes a trans-acylation reaction with a specific nucleophile in the AgrC receptor, and that this chemical step is required for activation (but not inhibition) of the agr response. It is also likely that the thiololactone unit limits the in vivo half-life of the peptide—the thiol ester linkage will undergo slow hydrolysis at physiological pH leading to the generation of an inactive linear peptide. The biological significance of this short-term in vivo efficacy is as yet unknown. It is equally unknown what role (if any) the recently reported 38 KDa RAP protein (Balaban et al. (1998) *Science* 280:438-440) plays in activation of the agr response by the secreted AgrD peptides.

Ready synthetic access to AgrD peptides represents an important step towards using the agr autoinduction system as a route to novel therapeutic agents. Indeed, the observation that it is possible to prepare novel synthetic AgrD variants which are capable of inhibiting but not activating the agr response is particularly significant in this regard. Moreover, the ability to easily adapt a solid-phase synthetic strategy to combinatorial-type synthesis is advantageous in the rapid identification of interesting compounds.

Experimental Procedures:

Biological activity of synthetic AgrD peptides. Biological assays were performed using groups I (RN6390B), II (SA502A) and III (RN8463) *S. aureus* strains (Ji et al. (1997) supra), each containing an agr P3-blaZ fusion plasmid (Novick et al. (1995) supra). Cells were grown in CYGP medium at 37° C. to either early exponential phase for agr activation studies, or midexponential phase for agr inhibition studies. To the cultured cells were then added one of the following: buffer solution (negative control), the appropriate cell supernatant containing the natural AgrD peptide as prepared as in (Ji, G., et al., 1995) (positive control) or the synthetic peptide solution in 20 mM tris.HCl buffer at pH 6.0. The cultures were then incubated at 37° C. with shaking for either 55 minutes (activation) or 80 minutes (inhibition) and β-lactamase activity then assayed using the nitrocefin spectrophotometric method modified as described in (Novick et al. (1995) supra) $ED_{50}$ and $IC_{50}$ values were extracted from the sigmoidal dose-response curves (e.g. FIGS. 2A-2B) using the program PRISM (GRAPHPAD Software Inc., San Diego, Calif.). All assays were performed in triplicate and the $ED_{50}$ and $IC_{50}$ values agreed to within ±10%.

Thioesterification Studies.

Initial studies involved selective thioesterification of a linear α-thiol acid peptide with 5,5'-dithiobis(2-nitrobenzoic acid) to give the S-(5-sulfenyl-2-nitrobenzoic acid) α-thiol ester derivative. This linear thiol ester precursor was then cyclized in solution through transthioesterification involving the cysteine sulfhydryl group. The overall yields using this strategy were poor, principally because of difficulties in selectively esterifying the α-thiol peptide.

Peptide Synthesis.

All peptides were synthesized manually according to the in situ neutralization/HBTU activation protocol for Boc SPPS (Schnolzer et al. (1992) supra). Thiololactone AgrD peptides were assembled on pre-loaded Boc-AA-[COS]-PEGA resins (Camarero et al. (1998) supra). Following chain assembly, peptides were treated with HF for 1 hour at 0° C. to give the corresponding fully unprotected peptide-[COS]-PEGA resins which were then washed with cold diethyl ether and then $CH_3CN/H_2O$ containing 0.1% trifluoroacetic acid. Unprotected peptides were chemoselectively cyclized and simultaneously cleaved from the support by swelling the beads in a mixture of 0.1 M sodium phosphate buffer at pH 7.0 and acetonitrile (80:20). After 12 hours, the beads were removed by filtration, washed with 0.1% trifluoroacetic acid in water and the peptides purified from the filtrate by reverse-phase HPLC.

Assembly of Peptides on Resin.

The peptide GVNAASSLF was assembled on an HS-PEGA resin (Camarero et al. (1998) supra) using Boc-SPPS. This corresponds to the AgrDII sequence with the single cysteine residue mutated to an alanine. Following synthesis and global deprotection, the peptide-[COS]-PEGA beads were swollen in a buffer containing 0.1 M sodium phosphate, pH 7.0 and ethanethiol (2% v/v), and the cleavage reaction allowed to proceed for 3 hours. The desired ethyl α thiol ester peptide was then purified from the supernatant by reverse-phase HPLC.

Protected Peptides

The protected peptides Z-Gly-Val-Asn-Ala-Ser($^t$Bu)-Ser(Bzl)-Ser(Bzl)-Leu-Phe and Z-Gly-Val-Asn-Ala-Dapa(Boc)-Ser(Bzl)-Ser(Bzl)-Leu-Phe corresponding to the Agr-DII sequence with a Cys5 to Ser mutation (lactone) and a Cys5 to Dapa (Diaminopropionic acid) (lactam) respectively, were synthesized on a Wang-resin using an Fmoc Nα protection strategy with HBTU activation protocols. Following chain assembly, the peptides were cleaved from the support and the Ser-5 or Dapa-5 side-chain deprotected by treatment with a trifluoroacetic acid:anisole:water mixture (90:5:5) for 4 hours. The partially protected peptide-α carboxylates were then dissolved in DMF (0.5 mg/mL) and treated with PyBOP (5 eq.) (and a catalytic amount of dimethylaminopyridine for the lactone precursor). The cyclization reaction was monitored by HPLC which indicated a period of 2 hours to be sufficient for complete reaction. The remaining protecting groups were then removed by treatment with HF and the desired peptides purified by reverse-phase HPLC and characterized by mass spectometry and 2D $^1$H NMR spectroscopy.

NMR

Two-dimensional $^1$H NMR spectra were measured on a Bruker DPX-400 spectrometer. Peptides were dissolved in either dimethylsulfoxide-d6 or 9:1 H2O/D2O pH 4.0 to a final concentration of 1-2 mM and a series of TOCSY (Bax et al. (1985) supra) and ROESY experiments recorded at 278 K. $^1$H resonances were assigned using standard procedures (Wuthrich (1986) supra).

Example 4

Transient Interference with Staphylococcal Quorum Sensing Blocks Abscess Formation Although there is a large body of information on the in vitro regulation of bacterial accessory genes involved in pathogenesis (referred to here as the virulon), the in vitro environment is highly artificial and applies only imperfectly, at best, to real-life situations. To date, however, most in vivo approaches have generated single point transcription profiles for infecting organisms but only a handful have addressed the expression pattern of virulence determinants through time, a critical feature of any infection (Shelburne and Musser (2004) *Curr. Opin. Microbiol.* 7, 283-9). The present inventors have begun to analyze temporal expression of staphylococcal virulence genes in vivo in animal models, and to compare the results with those obtained in vitro. To this end, real-time in vivo bioluminescent imaging has been employed to monitor the in vivo temporal expression of agr, a model virulence regulator in *Staphylococcus aureus* (recently reviewed by Novick (2003) *Mol. Microbiol.* 48, 1429-49).

As indicated herein above, Agr is a complex locus that controls expression of a substantial part of the staphylococcal virulon (Dunman et al. (2001) *J. Bacteriol.* 183, 7341-53; Recsei et al. (1986) *Mol. Gen. Genet.* 202, 58-61) consistent with its central role in pathogenesis (Abdelnour et al. (1993) *Infect. Immun.* 61, 3879-85; Booth et al. (1995) *Invest. Ophth. Vis. Sci.* 36, 1828-36; Cheung et al. (1994) *J. Clin. Invest.* 94, 1815-22; Gillaspy et al. (1995) *Infect. Immun.* 63, 3373-80). It consists of two divergent transcription units, driven by promoters P2 and P3 (Novick et al. (1995) *Mol. Gen. Genet.* 248, 446-58). The P2 operon contains four genes, agrB, D, C, and A, all of which are required for transcriptional activation of the agr system. AgrC is the receptor and AgrA the response regulator of a two-component signal transduction module that is autoinduced by a post-translationally modified small peptide (AIP) (Ji et al. (1997) *Science* 276, 2027-30; Ji et al. (1995) *Proc. Natl. Acad. Sci. USA* 92, 12055-9), processed by AgrB from the 46-residue agrD propeptide (Zhang et al. (2002) *J. Biol. Chem.* 277, 34736-42). The primary function of this four-gene unit is to activate the two major agr promoters, P2 and P3, significantly aided by a second regulatory protein, SarA (Chien and Cheung (1998) *J. Biol. Chem.* 273, 2645-52; Chien et al. (1998) *Mol. Microbiol.* 30, 991-1001). The actual effector of agr-dependent exoprotein gene regulation, however, is the P3 transcript RNAIII, which acts primarily at the level of transcription, by an unknown mechanism (Novick et al. (1993) *EMBO J.* 12, 3967-75). Being autoinduced, agr expression is population density-dependent and agr is therefore a quorum sensor.

Evolutionary divergence within the agr locus has given rise to multiple specificity groups, of which there are 4 in *S. aureus* (Ji et al. (1997) supra; Jarraud et al. (2000) *J. Bacteriol.* 182, 6517-22) and at least 20 others in non-*aureus* staphylococci (Dufour et al. (2002) *J. Bacteriol.* 184, 1180-6). A key feature of this diversity is that heterologous AIPs competitively inhibit agr activation by the cognate ligand (Lyon et al. (2002) *J. Biol. Chem.* 277, 6247-53). Indeed, a single dose of an inhibitory AIP, given along with the infecting bacteria, blocks the development of an experimental murine abscess which, in the absence of treatment, would mature 2-3 days later (Mayville et al. (1999) *Proc. Natl. Acad. Sci. USA* 96, 1218-23). This seems paradoxical since the AIP has a short lifetime—perhaps only 3 hours in vivo.

The present inventors have addressed this apparent paradox by means of an imaging system that enables the monitoring of bacterial gene expression during the course of an experimental infection. This system utilizes a highly sensitive CCD (charge-coupled device) camera to measure the bioluminescence from a luciferase-reporter carried by bacteria in vivo. Using this method, the present inventors have found that infecting bacteria grow rapidly during the first 3 hour, activating agr and producing toxic exoproteins. Thereafter, they enter a neutrophil-induced metabolic eclipse phase that lasts for 24-48 hours after which the abscess matures, accompanied by reactivation of bacterial metabolism. Administration of an inhibitory AIP delays agr activation for only 2-4 hours, but nevertheless, as noted, blocks formation of the abscess.

Since a sterile post-exponential supernatant from an agr+, but not from an agr− strain, causes a sterile lesion similar to the septic abscess, the evidence presented herein strongly suggests that the QS system must be activated during the first 3 hour. The present inventors conclude that a 3 hour delay is sufficient to block the production of toxic exoproteins and thus prevent the formation of an abscess.

Materials and Methods

Bacterial strains, plasmids and growth conditions. Bacterial strains and plasmids are listed in Table 2. Bacteria were routinely grown on GL media with appropriate antibiotics and in CYGP broth (Novick (1991) *Methods Enzymol.* 204, 587-683). Cell growth was monitored by a Klett-Summerson colorimeter with a green (540 nm) filter. Inocula for in vivo studies were prepared by growing cells from Klett 5 to Klett 50 (early exponential phase). The cells were harvested, washed and resuspended in PBS and stored at −80° C. for up to 4 weeks until used. Sterile culture filtrates from late exponential phase cells were prepared by growth of RN6734 and RN7206 in CYGP without glucose to Klett 400 followed by centrifugation and passage through a 0.2μ filter (Nalgene).

The $agrp_3$ and blaZ promoters were cloned by PCR from chromosomal DNA isolated from RN6734 and the staphylococcal β-lactamase plasmid, pI524 respectively into the shuttle plasmid, pMK4, carrying luxABCDE from *Photorhabdus luminescens*, optimized for expression in Gram-positive bacteria (Francis et al. (2000) *Infect. Immun.* 68, 3594-600). Promoter sequences were confirmed by dye terminator DNA sequencing chemistry (Skirball DNA Sequencing Core Facility). The AIP biosensor strain used for the mixed infection carries the $agrp_3$-lux fusion in RN7206 along with the group-II specific agrCA TCS (Lyon et al. (2000) *Proc. Natl. Acad. Sci. USA* 97, 13330-5). Plasmids were electroporated (Schenk and Laddaga (1992) *FEMS Microbiol. Lett.* 94, 133-8) into the *S. aureus* restriction deficient strain, RN4220 (Kreiswirth et al. (1983) *Nature* 305, 709-12), followed by electroporation or phage transduction into RN6734 and RN7206. Strains carrying the blaZp fusion also carried the β-lactamase control system on pI524. Plasmid retention was >95% after overnight growth in vitro in the absence of antibiotics and after recovery from 5-day-old lesions Murine subcutaneous abscess model. Groups (n=3 per variable examined) of hairless, euthymic SKH-1 (ISL) mice (Charles River) were used in the murine subcutaneous abscess model (Bunce et al. (1992) *Infect. Immun.* 60, 2636-40). In this model, staphylococci are injected subcutaneously with cytodex beads, and an abscess develops at the site of injection 2-3 days later, then sloughs and drains. The organisms grow rapidly initially, after which the population levels out and remains constant thereafter. Polymorphonuclear leuykocytes (PMNs) are attracted to the developing lesion by bacterial products and by pro-inflammatory cytokines, reaching maximum numbers by about 6 hours. In one report, about 50% of the organisms were shown to be phagocytized, whereas the rest remained extracellular (Ford et al. (1989) *J. Med. Microbiol.* 28, 259-66).

Bacteria were thawed, diluted to appropriate cell density, mixed with sterile cytodex beads (Sigma) and injected subcutaneously in a volume of 0.1 ml in the flank region. For agr inliibition studies, AIP-II (10 μg) in 5% DMSO in PBS or a control dose of 5% DMSO in PBS was mixed with the bacteria immediately prior to injection. For PMN depletion, cyclophosphamide (200 mg/kg) was injected intraperitoneally (ip) 4 days before infection and again 2 days before infection (Ford et al. (1989) supra). Blood harvested by retroorbital bleed immediately prior to infection was analyzed by flow cytometry in a FACSCALIBUR™ instrument (Becton Dickinson), which showed that the circulating PMN population was depleted by >95% with little or no effects on other circulating white blood cell populations. Mice were fed a standard diet ad libitum and monitored daily for signs of distress. Colony forming units (CFU) per abscess were determined by plating serial dilutions of excised lesions homogenized in PBS plus 0.5% Triton X-100.

Measurement of bioluminescence in vivo. Mice were imaged under isoflurane inhalation anesthesia as previously described (Francis et al. (2000) supra). Briefly, photons emitted from the bacteria were collected during a 1-minute to 5-minute exposure using the IVIS™ Imaging System and Living Image Software (Xenogen). Bioluminescent images were displayed using a pseudocolor scale (blue representing least intense and red representing the most intense signal) overlaid onto a gray-scale photographic image. For the bioluminescent images in the figures, the upper and lower limits of the overall bioluminescent signal collected by the CCD array are displayed in counts. For the graphs, the signal collected on a portion of the CCD array corresponding to the area of injected bacteria was determined in photons/sec/cm$^2$/sr, referred to as relative light units (RLU), and plotted vs. time after initiation of infection.

Determination of AIP-II half-life. To approximate the active lifetime of AIP, a synthetic version of AIP-IL (Lyon et al. (2002) *Biochemistry* 41, 10095-104) was incubated in PBS or rabbit serum at 37° C. for 4 hours. The sample was diluted and a dose-response assay for activation of β-lactamase induction of strain RN7206 carrying the agrCA-II $agrp_3$-blaZ reporter fusion was performed as previously described (Lyon et al. (2002) supra; Wright III et al. (2004) *Proc. Natl. Acad. Sci., USA*).

Results

Development and in vivo testing of the luciferase reporter system. Derivatives of several test strains were generated by introducing previously constructed staphylococcal plasmids containing, the agr P3 promoter ($agrp_3$) or the staphylococcal pI524-derived β-lactamase promoter (blaZp) transcriptionally fused to a modified version of the *Photorabdis* luciferase operon (Francis et al. (2000) supra). In this configuration, the luciferase operon directs the synthesis of the native luciferase substrate. In vitro, in agr+ host strains, the $agrp_3$ promoter shows classical mid-exponential agr induction (Vandenesch et al. (1991) *J. Bacteriol.* 173, 6313-20); in agr− strains the $agrp_3$ promoter is expressed very weakly throughout growth. The blaZp promoter is expressed at the same constant rate throughout growth in agr+ and agr− stains (Novick (1962) *Biochem. J.* 83, 229-235). To test the system in vivo, early exponential phase bacteria plus cytodex beads were injected subcutaneously into the flank region of hairless mice and the progress of the infection was followed in the living animals with the IVIS™ imaging camera (Contag et al. (1995) *Mol. Microbiol.* 18, 593-603). Initial tests were performed with graded bacterial inocula, from $10^6$ to $10^8$ organisms.

Figure 4A:
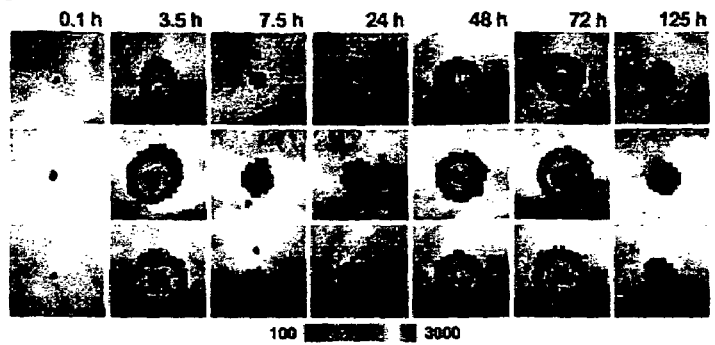
FIGS. 4A-E. Expression of agr during infection.
Figure 4B:
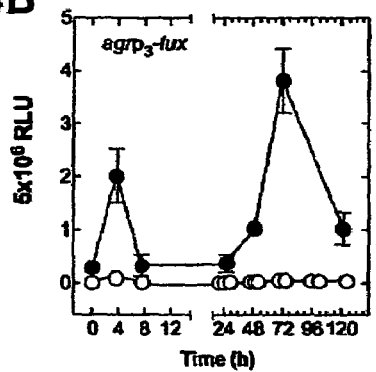
Figure 4C:
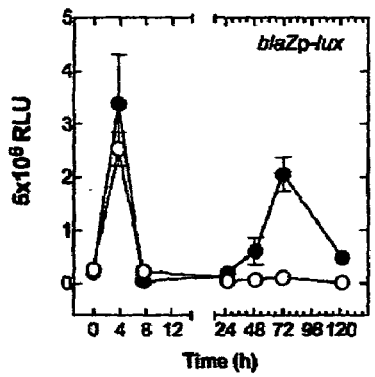
Figure 4D:
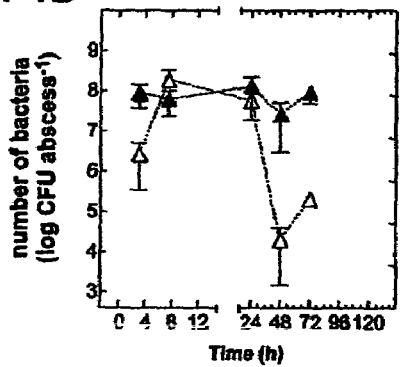

FIG. 4A shows a representative set of images of 3 different mice taken at various times following infection with of RN6734, an agr+ strain (agr-I) containing the $agrp_3$-lux fusion. As can be seen, there is very little signal immediately following infection. The signal then develops rapidly, reaching a peak by ~3 hours, and subsequently declines equally rapidly, remaining in an "eclipse" state for 36-48 hours, after which it sharply increases once again. The second activation peak probably represents renewed growth of the bacteria in the necrotic tissue associated with the abscess. The results for 3 mice are shown to illustrate reproducibility. In subsequent experiments, the present inventors usually used $10^8$ agr-I bacteria, which produced a visible subcutaneous lesion more reliably than lower inocula. The quantitative luciferase data obtained from these experiments are plotted in FIG. 4B, along with corresponding data for RN7206, an agr$^-$ but otherwise isogenic strain carrying the same agrp$_3$-lux fusion and for agr$^+$ and agr$^-$ bacteria carrying the blaZp-lux fusion (FIG. 4C). Predictably, comparisons within the first 6 hours show the rapid rise and decline of the agrp$_3$-lux signal for both agr$^+$ and agr$^-$ strains, with the signal amplitude of the latter amounting to about $\frac{1}{20}$ of the former and representing the basal activity of the agrp$_3$ promoter. The constitutive blaZp also showed this sharp rise and decline, with the same amplitude and the same magnitude for both agr$^+$ and agr$^-$ strains.

Agr trans-activation. Given the observed parallel between the agrp$_3$-lux and blaZp-lux signals during the first 3 hour, it was possible that the agrp$_3$-lux signal represented only growth of the bacteria and not specific agr activation. To test for specific agr activation a mixed infection strategy was used in which one of the infecting strains would generate a luciferase signal in response to AIP produced by the other (FIG. 5A). The responding strain, in effect, a biosensor, carried agrp$_3$-lux plus agrAC-II and the other was a wild-type agr-II strain. As shown in FIG. 5B, a strong luciferase signal was produced in the mixed infection with effectively the same kinetics as seen in mice singly infected with the wild-type strain carrying agrp$_3$-lux (FIG. 4A). Also shown are mixed infections with the biosensor plus either of two control strains—one producing AIP-I, the other producing no AIP. With either of the latter, only a weak signal representing the basal activity of the agrp$_3$-lux was observed. Note that this basal activity is not inhibited by an antagonistic AIP (Lyon et al. (2002) supra), so that similar signals are seen with the agr-null and agr-I co-infecting control strains. Since the bacteria were washed and since there was no immediate increase in the signal, it can be concluded that AIP-II was produced in vivo rather than being injected along with the bacteria. Thus, this response confirms the production and trans-activity of this peptide by the infecting bacteria.

Figure 5C:
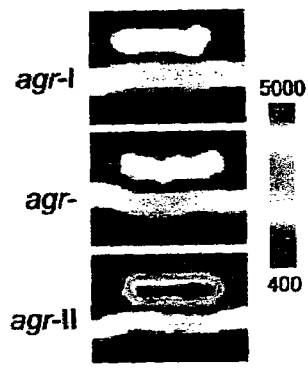
Figure 5C:
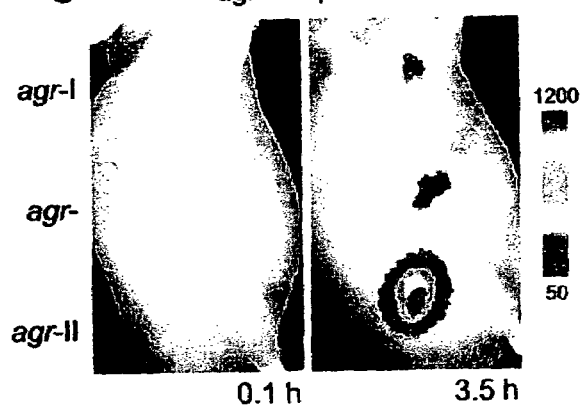
Figure 5C:
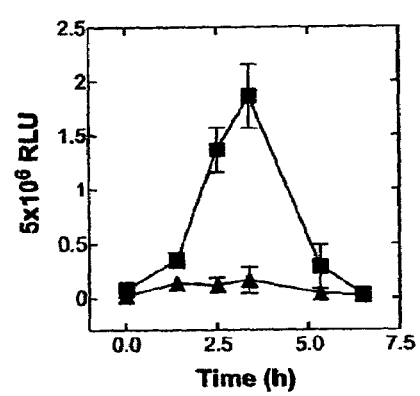
Figure 5D:
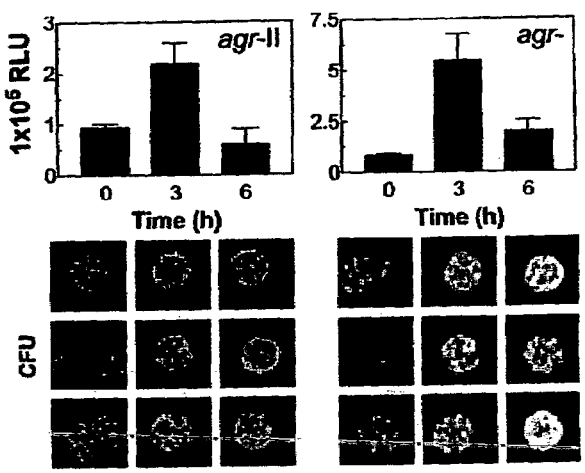

Effect of inoculum on agr activation kinetics. The present inventors next addressed the failure of agrp$_3$-lux to show the expected activation kinetics in vivo, despite the above demonstration of agr activation in trans. One possibility was that the high infecting dose was responsible. To test this, a more virulent strain, RN9130 (agr-II), was used that could reliably produce an abscess at a lower infecting dose than RN6734. After injection of $5 \times 10^6$ bacteria, containing either agrp$_3$-lux or blaZp-lux, the expected burst of agrp$_3$ activity was observed, about 10-fold greater than the increase in blaZp activity (FIG. 5C). The latter was nearly parallel to the clear increase in bacterial numbers (FIG. 5D), confirming the utility of blaZp-lux as a monitor of bacterial growth during this period. The difference in amplitude between agrp$_3$ and blaZp was not observed with an agr-null of RN9130 (RN9120). Aside from its clear activation of agrp$_3$, RN9130 at $5 \times 10^6$ showed temporal patterns of agrp$_3$ and blaZp activity almost identical to those of RN6734 at $10^8$.

The decline phase. Growth of agr$^+$ and agr$^-$ bacteria appears to level off after 3 hours, which may represent entry of the bacteria into stationary phase, as is normally observed in vitro. This is followed by a sharp decline in luciferase activity for both agrp$_3$-lux and blaZp-lux. Given that luciferase activity (catalyzed by LuxAB) is dependent on the endogenous synthesis of the luciferase substrate (by Lux-CDE) plus the required cofactors FMNH$_2$ and O$_2$, it is a sensitive indicator of the metabolic state of the organism (Contag et al. (1995) *Mol. Microbiol.* 18, 593-603) as well as a very sensitive reporter of transcription (and translation) activity and thus it seems likely that lack of substrate is responsible for the decline. A similar reduction in luciferase activity has been observed by the present inventors after bacterial growth has ceased on solid media. Bioluminescence is immediately restored by exogenous substrate or soon after the in vitro infusion of fresh media, suggesting a metabolic effect on substrate availability. Alternatively, immediate host responses to infection may be inducing a stress response which downregulates expression of agrp$_3$ and blaZp; the action of complement, acute-phase proteins in inflammatory fluids, or nitric oxide released by local host cells may represent candidate factors that exert this effect.

Figure 4E:
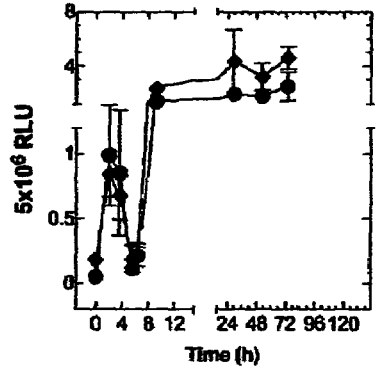

The eclipse phase: Effect of neutrophils. The eclipse period, which has not previously been described, was investigated next. Since viable counts of agr$^+$ bacteria taken from the lesions during this time showed no decrease (FIG. 4C), consistent with previous studies using this model (Ford et al. (1989) supra; Molne et al. (2000) *Infect. Immun.* 68, 6162-7), the eclipse cannot be accounted for by loss of bacterial viability. The present inventors propose that the eclipse represents metabolic shutdown, perhaps owing to phagocytosis by PMNs attracted to the site of infection. Measurements of luciferase activity at intervening time points (9.5 and 19.5 hours) showed the same very low activities as depicted in FIG. 4. It is conceivable, but unlikely, that promoter activation occurs between these time points. It has been reported, however, that that the numbers of PMNs recruited to the site of infection in this model are maximal at six hours (Ford et al. (1989) supra), corresponding to the onset of the eclipse period. To test for a possible role of PMNs, infected mice were rendered neutropenic by treatment with cyclophosphamide. In FIG. 4E is shown the kinetics of luciferase production by RN6734 carrying agrp$_3$-lux or blaZp-lux in neutropenic mice. As shown therein, the same initial rise and decline of activity of both agrp$_3$ and blaZp is observed, as seen with normal mice, but there is no eclipse. Both signals rapidly rise again to a high plateau and remain there for the next 2 days. This reactivation may be due to the availability of nutrients provided by the influx of inflammatory fluids in response to the Thus the PMNs appear to be responsible for the eclipse, but not for the sharp decline in luciferase activity after the initial rise, since this evidently precedes the arrival of PMNs at the infection site. If, indeed, the eclipse phase is due to metabolic shutdown by the PMNs, then one would ask how this happens. Previous studies with this model suggest that some 50% of the bacteria have been ingested by PMNs at this point during the progress of the infection (Ford et al. (1989) supra), that virulent *S. aureus* survive intracellularly (Gresham et al. (2000) *J. Immunol.* 164, 3713-22), and that PMNs obtained from an abscess are unable to kill *S. aureus* (Finlay-Jones et al. (1991) *J. Med. Microbiol.* 34, 73-81). In contrast, agr$^-$ staphylococci are rapidly eliminated in vivo, as previously reported (Chan et al. (1998) *J. Bacteriol.* 180, 6082-3673) and confirmed here (FIG. 4D), and they failed to form an abscess or to reactivate agrp$_3$ or blaZp at 48-72 hours (FIGS. 4B and C). Studies are currently in progress to determine the effects of phagocytosis by PMNs and of PMN-related host factors on the metabolic activity of bacteria in relation to the eclipse phase. Temporary residence within phagocytes is, incidentally, thought to be partly responsible for the refractoriness to antibiotics of staphylococci in an abscess (Bamberger et al. (2002) *Antimicrob. Agents Chemother.* 46, 2878-84; Vesga et al. (1996) *J. Infect. Dis.* 173, 739-42). Metabolic shutdown would presumably contribute importantly to this refractoriness.

Figure 6A:
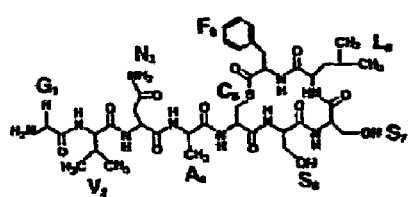
FIGS. 6A-E. In vivo and in vitro consequences of agr inhibition by a synthetic QS peptide antagonist.
Figure 6B:
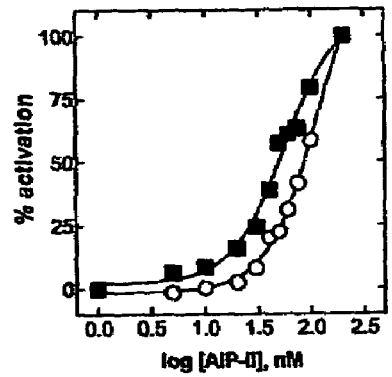
Figure 6C:
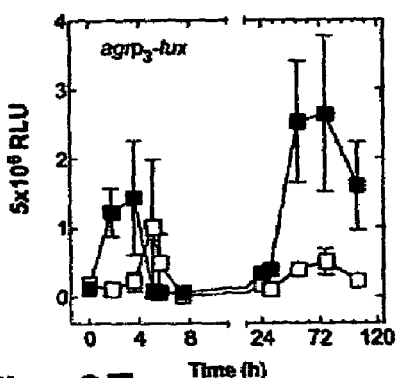
Figure 6D:
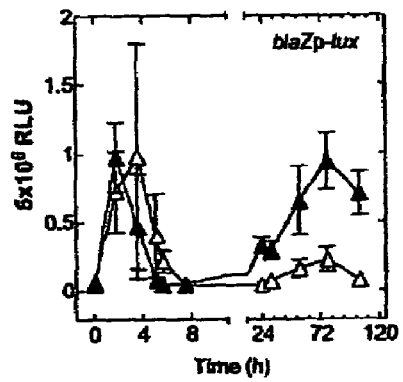
Figure 6E:
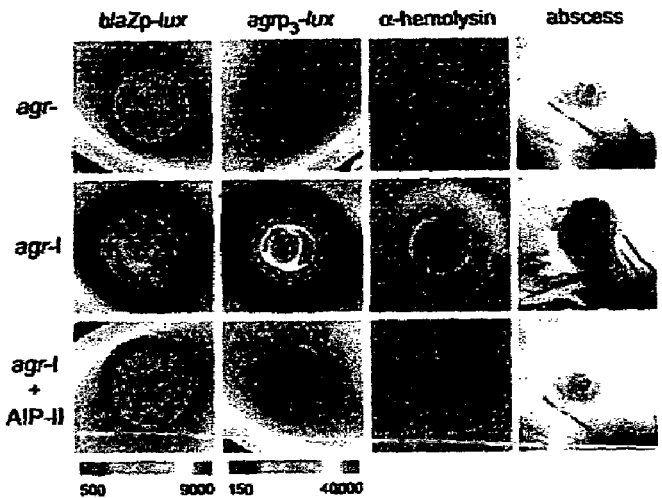

The single-dose paradox. These results together have set the stage for an understanding of the long-term effects of a single dose of an antagonistic AIP. A single dose of an antagonist AIP-II (FIG. 6A) co-injected with the agr-I bacteria blocks the subsequent formation of an abscess (Mayville et al. (1999) supra); under these conditions agr activation is inhibited for some 3 hours but not eliminated (FIG. 6C), whereas blaZp activation is not significantly affected (FIG. 6D). This result suggests that the effective biological lifetime of the peptide in vivo is about 3 hours. As expected, this is considerably shorter than the in vitro lifetime (~4 hours in normal rabbit serum, see FIG. 6B), since the AIP is inherently unstable at physiological pH, would almost certainly be cleared by the kidneys, and might be degraded by thioesterases, peptidases or inactivated by phagocyte-derived NADPH oxidases (Rothfork et al. (2004) *Proc. Natl. Acad. Sci. USA* 101, 13867-72). A remarkable conclusion from this experiment is that the transient (~3 hour) inhibition of agr activation by the inhibitory AIP was sufficient to attenuate abscess formation and to prevent the agr and blaZ re-activation, all of which occur 36-48 hours later. In other words, agr-dependent events occurring within the first 3 hours are necessary (and probably sufficient) for the subsequent development of an abscess in this model system. Notably, the inhibitory AIP acts similarly on solid media in vitro, blocking the luciferase activity of the agrp$_3$-lux construct and agr-induced α-hemolysin production without affecting blaZp-lux expression (FIG. 6E).

Components of the agr-triggered virulon cause a sterile abscess. The activation of agr-I, when blocked by AIP-II, is not only delayed, but is also weaker than in the absence of any inhibitory peptide. More importantly, the delayed activation occurs at about the same time that the eclipse period starts. It will be recalled that at least some of the agr up-regulated virulence factors are produced as long as 2 hours after agrp$_3$ activation in vitro (Vandenesch et al. (1991) supra); thus, if the eclipse involves these factors, then they would probably not be produced following the delayed activation of the agr system. That is, the antagonistic AIP delays production of the abscess-inducing factors for just long enough to enable the PMNs to take over.

To test for a role of agr-induced factors (exoproteins), sterile supernatant from post-exponential cultures of agr$^+$ (agr-I) and agr$^-$ strains instead of viable bacteria were injected into mice. As can be seen in FIG. 7A, there is a dramatic difference in exoproteins elaborated by these strains. Remarkably, the agr$^+$ supernatant produced a sterile lesion superficially very similar, although less well demarcated, and having the same kinetics as viable agr$^+$ organisms (FIG. 7B). This effect was observed previously using supernatants from uncharacterized strains (Parker (1924) *J. Exp. Med.* 40, 761-772). Neither the agr$^-$ nor a boiled agr$^+$ supernatant produced a detectable lesion. To compare the septic and sterile lesions microscopically, several mice were sacrificed and histological sections were prepared therefrom. As shown in FIG. 7C, the septic abscess consists of large numbers of PMNs, Gram-positive cocci, plus local tissue necrosis, whereas the sterile lesion lacks the easily identified cocci. This finding is consistent with the conclusion that agr-induced exoproteins are responsible for the abscess and are not made in sufficient quantities when agr expression is blocked, even temporarily, by an AIP antagonist or is eliminated by disruption of the agr locus.

Discussion

The results presented herein delineate the natural history of staphylococcal abscess formation in terms of the temporal pattern of agr expression. Entry of a relatively small number of staphylococci into the subcutaneous tissue of the mouse leads to rapid growth and activation of the agr QS system (~3 hours) and is followed by an equally rapid decline (~7 hours). The decline in activity likely represents entry of the bacteria into the stationary phase or metabolic inhibition by host factors and is independent of PMNs since it occurs in neutropenic mice. A PMN-dependent metabolic eclipse period ensues, lasting for (~48 hours), during which agr$^-$ bacteria are killed and agr$^+$ bacteria form a lesion. This is followed, with agr$^+$ but not with agr$^-$ organisms, by the re-activation of both promoters and the maturation of the abscess (~48-72 hours). Administration of an inhibitory AIP along with the bacteria transiently inhibits agr (but not blaZ) activation and blocks subsequent formation of the lesion. The inhibitory effects of the antagonistic AIP last just long enough for the PMN-induced eclipse to be initiated. Since *S. aureus* supernatant is cytotoxic to PMNs in vitro (Haslinger et al. (2003) *Cell. Microbiol.* 5, 729-41), the present inventors propose that the early production of exoproteins may establish an inhospitable environment for the incoming PMNs, and cause the influx of tissue fluids. This could enhance survival of extracellular and ingested bacteria and provide a new source of nutrients, facilitating later reactivation.

A fundamental conclusion from these studies is that a rapid burst of agr activity early in infection, perhaps before the innate immune system has had time to assemble a response, is critical for later survival of the bacteria in host tissues. These results may provide a biological rationale for QS activation of the staphylococcal virulon, namely a requirement for large quantities of the toxic exoproteins in order to neutralize the killing function of the PMNs and enable the development of the characteristic staphylococcal lesion. If the virulon were activated immediately following entry, for example, by the elevated temperature of the mammalian body, then the innate immune response might be mobilized before there was a sufficient quantity of exoproteins to counter its effects, and the organisms would be eliminated. Both agr$^+$ and agr$^-$ bacterial multiply rapidly before PMNs are mobilized (see FIG. 5D); agr$^+$ organisms then undergo autoinduction of the virulon, resisting killing by the influx of PMNs, while the agr$^-$ organisms are eventually eliminated. In support of this concept, which has also been articulated by Hentzer and Givskov (Hentzer and Givskov (2003) *J. Clin. Invest.* 112, 1300-7), the present inventors have observed that administration of an agr$^+$ supernatant along with agr$^-$ organisms protects the bacteria, which later persist in the septic abscess.

Recent reports have suggested that agr is not expressed in vivo and is not relevant for pathogenesis. The results described herein are clearly inconsistent with these reports, but these inconsistencies are explicable. Yarwood et al. (2002) *J. Bacteriol.* 184, 1095-101) report that stationary phase cells of *S. aureus* strain MN-NJ introduced into a sterile subcutaneous chamber in rabbits rapidly turn off agr RNAIII expression. The present inventors have determined that early stationary phase cells, which are maximally induced for RNAIII, rapidly turn off RNAIII synthesis following dilution into fresh medium and similarly switch off RNAIII production following injection into mice. Goerke et al. report that staphylococci extracted from subacute or chronic lesions contain very low levels of RNAIII. Of note, these organisms were isolated from sputa of chronically *S. aureus*-infected CF patients (Goerke et al. (2000) *Infect. Immun.* 68, 1304-11) or 2-6 days after experimental infection (Goerke et al. (2001)

Mol. Microbiol. 40, 1439-47). In other words, the organisms were isolated long after initiation of the infection. The present inventors have demonstrated that agr expression is critically required for events early in infection. In that Goerke et al. did not collect any samples until 2 days after the initiation of their foreign body infection, they would not have observed any early activation stages. Also, since agr activity is critically dependent on the metabolic activity of the organism, it would probably not have been seen in organisms from the chronic CF lung because these would probably not be metabolically active. Therefore, the results of Goerke et al. are consistent with the eclipse concept, and are not relevant to the well-established essentiality of agr for staphylococcal pathogenicity. Notably, a similar shift from high to low metabolic state has been reported for experimental foreign body *S. epidermidis* infections (Vandecasteele et al. (21004) *J. Bacteriol*. 186, 2236-9).

An interesting contrast with the observations reported here exists with *S. aureus* strains producing the agr-regulated superantigen, toxic shock syndrome toxin-1 (TSST-1). Local infections caused by these organisms are remarkably apurulent (Fast et al. (1988) *J. Immunol*. 140, 949-53; Kreiswirth et al. (1986) *Ann. Intern. Med*. 105, 704-7), owing to the repression of exoprotein genes by the agr-induced superantigen (Vojtov et al. (2002) *Proc. Natl. Acad. Sci. USA* 99, 10102-7). Thus the regulatory behavior of TSST-1 serves to illustrate an agr-dependent pathogenic strategy that is radically different from that used for abscess formation, which involves production of large quantities of exoproteins. Moreover, TSST-1 is encoded by a highly mobile pathogenicity island (Lindsay et al. (1998) *Mol. Microbiol*. 29, 527-43). Thus, the agr QS system represents a fundamental regulatory paradigm that can encompass different adaptive strategies and can accommodate horizontally acquired virulence determinants.

Experimental results presented herein significantly enhance our understanding of the role of staphylococcal QS and of PMNs in the pathogenesis of a typical staphylococcal lesion.

This invention may be embodied in other forms or carried out in other ways without departing from the spirit or essential characteristics thereof. The present disclosure is therefore to be considered as in all respects illustrative and not restrictive, the scope of the invention being indicated by the appended Claims, and all changes which come within the meaning and range of equivalency are intended to be embraced therein.

What is claimed is:

1. A method for treating a *Staphylococcus aureus* (*S. aureus*) infection in a subject comprising administering to the subject an effective amount of a cyclic peptide, and at least one antibiotic, effective to treat the infection, said cyclic peptide comprising the structure:

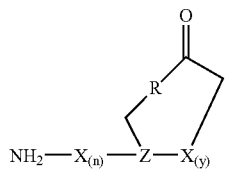

Wherein X is selected from the group consisting of an amino acid, an amino acid analog, a peptidomimetic and a non-amide isostere, Z is selected from the group consisting of a synthetic amino acid and a biosynthetic amino acid, R is selected from the group consisting of oxygen, nitrogen, sulfur and carbon, n is 0-10 and y is 1-10, wherein said cyclic peptide is administered in an effective amount to achieve a clinically significant reduction in said *S. aureus* infection.

2. The method of claim 1, wherein said cyclic peptide and said antibiotic are administered via different routes.

3. The method of claim 1, wherein said cyclic peptide and said antibiotic are administered via the same route.

4. The method of claim 1, wherein Z has a side chain comprising oxygen, nitrogen or carbon.

5. The method of claim 1, wherein the cyclic peptide inhibits the accessory gene regulator (agr) response.

6. The method of claim 1, wherein y is 4.

7. The method of claim 6, wherein the peptide is selected from from the group of peptides consisting of SEQ ID NO: 1, SEQ ID NO: 2, SEQ ID NO: 3, SEQ ID NO: 4, SEQ ID NO: 5, SEQ ID NO: 6, SEQ ID NO: 7 and SEQ ID NO: 8.

8. The method of claim 1, wherein a composition is administered and said composition comprises said peptide, at least one antibiotic and a carrier.

9. The method of claim 1, wherein a pharmaceutical composition is administered and said pharmaceutical composition comprises said peptide, at least one antibiotic and a pharmaceutically acceptable carrier.

10. The method of claim 9, wherein the carrier is selected from the group consisting of a diluent, an aerosol, a topical carrier, an aqueous solution, a nonaqueous solution, and a solid carrier.

11. The method of claim 1, wherein said *S. aureus* infection causes a site of localized infection, said method comprising draining the site of localized infection to produce a treated site prior to administering said cyclic peptide directly to said treated site.

12. The method of claim 11, wherein said at least one antibiotic is administered directly to the treated site.

* * * * *